(12) United States Patent
Hancock

(10) Patent No.: US 9,050,115 B2
(45) Date of Patent: Jun. 9, 2015

(54) SURGICAL ANTENNA

(75) Inventor: Christopher P. Hancock, Avon (GB)

(73) Assignee: CREO MEDICAL LIMITED, Wales (GB)

( * ) Notice: Subject to any disclaimer, the term of this patent is extended or adjusted under 35 U.S.C. 154(b) by 1251 days.

(21) Appl. No.: 12/311,571

(22) PCT Filed: Oct. 10, 2007

(86) PCT No.: PCT/GB2007/003828
§ 371 (c)(1),
(2), (4) Date: Oct. 23, 2009

(87) PCT Pub. No.: WO2008/044000
PCT Pub. Date: Apr. 17, 2008

(65) Prior Publication Data
US 2010/0030207 A1    Feb. 4, 2010

(30) Foreign Application Priority Data

Oct. 10, 2006 (GB) .................................. 0620060.4
Jul. 17, 2007 (GB) .................................. 0713899.3

(51) Int. Cl.
*A61B 18/04* (2006.01)
*A61B 18/18* (2006.01)
*A61B 17/3211* (2006.01)

(52) U.S. Cl.
CPC ............. *A61B 18/18* (2013.01); *A61B 17/3211* (2013.01); *A61B 18/1815* (2013.01)

(58) Field of Classification Search
CPC ............... A61B 2018/1815; A61B 2018/1823; A61B 2018/183; A61B 2018/1838; A61B 2018/1846; A61B 2018/1853; A61B 2018/1861; A61B 2018/1869; A61B 2018/1876; A61B 2018/1884; A61B 2018/1892

USPC ....................... 606/44, 46; 607/101, 105, 156
See application file for complete search history.

(56) References Cited

U.S. PATENT DOCUMENTS

| 4,534,347 | A | * | 8/1985 | Taylor ............................. 606/33 |
| 4,700,716 | A | * | 10/1987 | Kasevich et al. ............. 607/156 |
| 4,848,362 | A | * | 7/1989 | Larsen ............................ 607/98 |
| 5,150,717 | A | * | 9/1992 | Rosen et al. .................. 607/156 |
| 5,152,286 | A | * | 10/1992 | Sitko et al. ...................... 607/45 |

(Continued)

FOREIGN PATENT DOCUMENTS

| EP | 0919196 | * | 6/1999 | ............. A61B 17/36 |
| WO | WO 2004/047659 | | 6/2004 | |

(Continued)

*Primary Examiner* — Jaymi Della
(74) *Attorney, Agent, or Firm* — Arent Fox LLP

(57) ABSTRACT

A surgical instrument (100) (e.g. scalpel) is disclosed which has an antenna arranged to emit a substantially uniform microwave radiation field (e.g. having a frequency of 5-100 GHz) at an edge of a cutting element (110) (e.g. blade). The emitted radiation can cauterize tissue e.g. broken blood vessels simultaneously with cutting. The antenna may be integral with the cutting element, e.g. a metallized piece of ceramic attachable at an end of a waveguide (120, 150) to receive radiation therefrom. The cutting element (110) can include a quarter wave transformer to couple power efficiently from the waveguide (120). The instrument can be used with impedance matching apparatus to control the energy delivered into the tissue. Also disclosed is an invasive ablation probe (e.g. insertable through a catheter) having a plurality of radiating elements whose emitted field combine to give a uniform effect at an insertion end of the probe.

12 Claims, 24 Drawing Sheets

(56) References Cited

U.S. PATENT DOCUMENTS

| | | | |
|---|---|---|---|
| 5,314,466 A * | 5/1994 | Stern et al. | 607/156 |
| 5,364,392 A * | 11/1994 | Warner et al. | 606/34 |
| 6,097,985 A * | 8/2000 | Kasevich et al. | 607/102 |
| 7,118,590 B1 * | 10/2006 | Cronin | 607/105 |
| 2002/0156511 A1 | 10/2002 | Habib | |
| 2005/0143795 A1 | 6/2005 | Habib et al. | |
| 2006/0047274 A1 | 3/2006 | Habib et al. | |
| 2006/0069402 A1 * | 3/2006 | Sugimura | 606/166 |
| 2006/0293651 A1 * | 12/2006 | Cronin | 606/33 |
| 2007/0016180 A1 * | 1/2007 | Lee et al. | 606/33 |
| 2007/0270924 A1 * | 11/2007 | McCann et al. | 607/99 |
| 2010/0228244 A1 * | 9/2010 | Hancock et al. | 606/33 |

FOREIGN PATENT DOCUMENTS

| | | | | |
|---|---|---|---|---|
| WO | WO 2005/030071 | | 4/2005 | |
| WO | WO 2005/115235 | | 12/2005 | |
| WO | WO 2005115235 A1 * | | 12/2005 | A61B 5/05 |

\* cited by examiner

Voltage Distribution

Farfield Pattern

SURGICAL ANTENNA

CROSS-REFERENCE TO RELATED APPLICATION

This application is a National Stage entry of International Application No. PCT/GB2007/003828, having international filing date of Oct. 10, 2007, which claims priority to GB Patent Application No. 0620060.4 filed Oct. 10, 2006, and GB Patent Application No. 0713899.3 filed Jul. 17, 2007, the disclosure of each of which is hereby incorporated in its entirety by reference.

TECHNICAL FIELD

The current invention relates to surgical antennas which are adapted to controllably deliver energy into biological tissue.

BACKGROUND TO THE INVENTION

Excessive blood loss when performing surgery on highly vascularised organs within the human or animal body is a particular problem when using conventional surgical tools, such as the scalpel blade.

The liver is the largest internal organ in the body and is a lobed glandular organ contained in the abdomen. The main role of the liver is in the processing of products of digestion into substances useful to the body. It also neutralises harmful substances in the blood, secretes bile for the digestion of fats, synthesises plasma proteins, and stores glycogen and some minerals and vitamins. When the liver becomes diseased or cancerous, it may be necessary to remove sections of the liver or kill the cancerous cells in situ in order to cure the patient. One of the risks or drawbacks associated with conventional liver surgery is the large amount of blood that is lost during surgery. For example, it has been reported that the average blood loss during the long and complex surgery to remove liver tumours is anything between 2 and 20 pints.

The extent to which the liver may bleed when it is cut can lead to morbidity and mortality as well as presenting visibility problems to the surgeon as he or she attempts to controllably cut into the organ.

Liver cancer or hepatic carcinoma is a significant cause of death worldwide. In the United States alone, over 18,000 people are diagnosed with new primary liver tumours each year. Surgical removal of the cancerous tumour and a region of surrounding tissue is currently the treatment of choice and liver resection is generally considered to be the only potentially curative treatment for primary and metastatic liver tumours.

One known device that attempts to address the above problems consists of four needle antennas arranged in a formation whereby the four antennas are inserted into the liver tissue and connected to a RF frequency generator (having frequency range of between 480-700 kHz) such that the tissue surrounding the needles is heated to seal the blood vessels. This provides a dry edge that is subsequently cut to remove the tumour or the diseased section or segment.

SUMMARY OF THE INVENTION

Expressed generally, the invention provides a surgical antenna that is associated with a cutting blade, wherein the antenna is arranged to controllably deliver microwave energy to a region where the blade cuts through the tissue. The microwave energy can coagulate blood to effectively seal off the blood flow at the region. Furthermore, the antenna may also be used to treat large cancerous tumours within the liver or any other highly vascularised organ by instantly heating the cancerous cells to a temperature that causes cell necrosis, but prevents tissue charring and minimises damage caused to healthy tissue around the tumour.

Thus, the invention may provide a device that can simultaneously coagulate (or seal) and efficiently cut tissue, thereby being capable of reducing or minimising blood flow or preventing excessive blood loss. This operation is in contrast with the conventional devices, where the cutting process to remove the diseased section from the healthy section is performed subsequent to the ablation process.

This invention is of particular interest for solid organ surgery on highly vascularised organs or tissue structures. The invention may also be used to treat cancerous tumours where it is required to ablate solid tumours that are present in large organs, within the human body, for example, the liver or the lungs. The current invention harnesses the advantages of using high frequency microwave radiation to localise the zone of ablation and create a high enough energy density in said localised zone to instantly heat the tissue to cause effective thermal ablation or cauterisation. These features can provide an advantage in both resection and tumour ablation applications.

Accordingly, a first aspect of the invention may provide a surgical instrument having a cutting element having an edge for cutting biological tissue; and an antenna arranged to emit a substantially uniform microwave radiation field at the edge of the cutting element. The field may be emitted whilst simultaneously cutting, thereby providing sealing (cauterising) radiation instantly. Preferably, the antenna is arranged to emit the field along the edge of the cutting instrument. The antenna preferably includes a feed structure for connecting to a source of microwave radiation, and a radiating portion arranged to emit the radiation field. The cutting element may include the radiating portion, and may include a coupling portion for receiving energy from the feed structure. Preferably, the coupling portion is adapted such that the cutting element receives a substantially maximum field coupling from the feed structure. The cutting element may have a metallised surface except at the proximal coupling portion and the distal radiating portion.

The feed structure may include a waveguide, e.g. loaded with the cutting element.

The antenna may include a plurality of radiating elements, e.g. a plurality of cutting elements attached side by side to increase the length of a cutting blade of the instrument. Alternatively, a plurality of patch antennas may be fabricated on a single cutting element in proximity to the edge. The feed structure preferably includes a power splitter arranged to split power from a single source of microwave radiation evenly between each of the plurality of radiating elements.

The antenna structure of the invention may be adapted for use in liver resection, where it is required to remove sections of the liver without causing excessive blood loss. Said sections (or sectors) of the liver may be cancerous or may be diseased or damaged, due to, for example, excessive alcohol intake. Preferably, the frequency of radiation is selected to provide a substantially uniform field at the cutting region, and, more preferably, to provide a depth of penetration by radiation where damage to healthy tissue is limited. The depth of penetration is defined here as the point (or distance) at which the energy is reduced to 37% of the value at the distal tip of the antenna (the aerial). This is of particular significance for liver treatment, where it is important to preserve as much of the liver as possible to enable the organ to successfully regenerate.

Preferably, the antenna is incorporated into the cutting blade to form a radiating blade structure. Thus, the sharp edge of the radiating blade may perform the cutting action while the microwave energy may perform the function of coagulating or sealing highly perfused tissue structures as the blade cuts through the tissue to prevent blood loss.

Preferably, the field profile of the radiated microwave energy is concentrated at or around the cutting edge of the blade and is directed into the tissue structure.

The use of high microwave frequencies (defined here as 10 GHz or higher) offers particular advantage over the use of lower microwave frequency systems due to the limited depth of penetration of the energy by radiation and the ability to enable small sharp blade structures to efficiently radiate energy into the tissue to seal off blood flow by being able to produce uniform fields along the length of the blade whilst at the same time being capable of cutting through the tissue to remove sections of diseased or cancerous tissue. The higher the microwave frequency, the more localised the energy distribution becomes and the energy density at the site where the cutting action takes place is correspondingly high, hence the easier it becomes to effectively seal off blood flow as the cutting blade is introduced into highly perfused biological tissue structures. A substantially uniform field profile can enable uniform coagulation or other tissue effects along the cutting edge. Using lower frequency microwave energy (e.g. 1 GHz or less) can lead to non-radiating regions of the antenna, which reduces the ability of the device to produce effective coagulation. By emitting a uniform field of microwave energy having a suitable energy density along the edge of the blade, the wound is effectively sealed as the surgeon cuts through the tissue structure. This invention may revolutionise surgery on highly vascularised organs within the human body.

The antenna structures which exhibit the cutting/sealing aspect of the invention disclosed above may also be used for ablating biological tissue, e.g. to enable controlled and focussed ablation of cancerous tumours within the liver. In this aspect of the invention, use is made once again of the ability to produce localised or focussed microwave energy, but in this instance, a plurality of radiating elements are used to spread the energy distribution.

Furthermore, the antenna structures disclosed herein may be used to obtain information concerning the structure of biological tissue e.g. to differentiate between tissue types, and/or to identify various types of cancerous tumours, and/or to determine the stage of tumour growth, and/or to control associated electronic instrumentation to enable the radiating section of the surgical antenna to be impedance matched to the complex impedance of the biological tissue to enable maximum power transfer between an energy source and the biological tissue being treated or resected. This latter feature may be of particular interest during the liver resection process because of the need to efficiently launch energy into liver tissue and blood. These two loads differ in impedance value. This change in impedance implies that there will be a change in impedance match between the radiating blade and the load, thus a portion of the power will be reflected back along the energy delivery cable.

In this specification microwave means the frequency range of between 5 GHz and 100 GHz, but preferably between 10 GHz and 25 GHz, and even more preferably between 14 GHz and 22 GHz. For example, spot frequencies of 14.5 GHz or 24 GHz may be used.

Higher frequencies (e.g. 24 GHz) may provide advantages such as a smaller size waveguide cable assembly, a smaller size antenna and smaller depth of penetration than lower frequencies (e.g. 14.5 GHz). For example, in liver at 24 GHz the depth of penetration is 1.1 mm, whereas it is 2 mm at 14.5 GHz. The smaller depth of penetration may permit higher energy density and more instant seal or coagulation to take place as the blade cuts into the tissue.

The antenna may comprise any one of a loaded waveguide structures, a microstrip antenna type structure and a co-axial structure. Preferably, the antenna structure includes means for increasing the size of the energy profile to enable large volume tissue ablation of solid tumours.

The present invention may also be used to treat the spleen. The spleen is an abdominal organ involved in the production and removal of blood cells in most vertebrates and forms part of the immune system. Specific embodiments of the surgical antennas described here may be used to perform splenectomies to remove injured portions of the spleen or to coagulate lacerations.

However, the antenna structures introduced here are not limited to being used for liver resection, liver tumour ablation or splenectomies and may be used to treat other organs where the energy profile generated by the antenna and the physical shape of the antenna offers advantages over existing treatment methods and systems.

The present invention may provide the following advantages:

high frequency microwave energy can enable the volume of active heating to be localised in accordance with the depth of penetration of the energy, which results in fast heat generation and allows microwave energy to overcome the heat-sinking effects of perfusion, the radiating portion of the antenna (the aerial) may be dynamically impedance matched to the impedance of the biological tissue being treated, which allows energy to be efficiently delivered into the tissue to provide instant and controllable tissue ablation or cauterisation, the depth of penetration by radiation is limited, which may result in controlled tissue destruction, there is no need for external ground pads to provide a return current path, which can reduce the complexity associated with setting up the system and prevent superficial skin burns that may be caused when a return pad makes an intermittent contact with the surface of the skin, energy delivery does not stall due to the external return pad making a poor contact with surface of the skin or due to the pad falling off or being pulled off, there is no need for a bipolar antenna arrangement or the use of saline to produce a localised conduction path, thus a single cutting/resecting antenna or a tumour ablation antenna may be used, and since the microwave energy can effectively 'seal' an open wound, the invention may help to prevent or minimise the chance of post operative infection occurring.

Due to the fact that biological tissues are lossy dielectrics, they absorb large amounts of the microwave energy produced by the radiating antenna. In human tissues both the conductivity and relative permittivity depend highly on frequency and temperature and so it is advantageous to use high microwave frequencies for the identified applications associated with the current invention.

In one embodiment, the radiating section of the antenna structure may be dynamically tuned or impedance matched to the changing tissue load impedance (i.e. the distal tip of the radiating blade or structure may be adjusted to be the complex conjugate of the complex impedance of the treatment tissue)

in order to optimise the power delivered into the tissue and to minimise reflections. Additionally or alternatively, the antenna may be arranged to enable measurements of tissue characteristics to be taken. For example, the antenna may be used with a treatment system as disclosed in WO2004/047659 or WO2005/115235. However, the invention is not limited to use in these electrosurgical systems, but could also be used in other electrosurgical treatment and/or measurement systems. For example, the invention may be used without tissue measurement or dynamic impedance matching circuitry, i.e. it may be connected to a system that provides a microwave source with the provision to adjust the power level and the delivery time (e.g. variable pulse duration) only. Preferably, a single frequency source oscillator and a solid state amplifier unit is used to produce the microwave energy.

Accordingly, in a second aspect, the invention may provide surgical cutting apparatus having a microwave radiation source arranged to generate microwave radiation; a surgical instrument according to the first aspect above; a reflected radiation detector connected between the source and the cutting instrument; and an impedance adjuster connected between the source and the cutting instrument; wherein the reflected radiation detector is arranged to detect the magnitude and phase of microwave radiation reflected back through the instrument towards the source, and the impedance adjuster has an adjustable complex impedance that is controllable based on the detected magnitude and phase of the reflected microwave radiation.

In one embodiment, the invention provides a waveguide antenna structure having a hard ceramic material for the radiating element (the aerial) and the sharp blade. In another preferred embodiment, the invention provides a microstrip antenna structure having a plurality of patch antennas disposed onto the end of a sharp blade. For the latter embodiment, the patch antennas may be disposed on a first side of the tip of a sharp blade, wherein the second side of the blade is completely metallised to form a ground plane. In such an arrangement, the antenna feed structure may also be disposed on the same side as the radiating patches. Tri-plate or stripline microwave structures may be used, especially for liver resection.

The choice of frequency may be influenced by one or more of the following factors: the ability to produce a controlled depth of penetration by radiation into the tissue, being able to generate uniform tissue effects (coagulation) along the edge of a dual radiating and cutting blade, being able to generate enough power (energy) at the surface of the radiating blade to effectively coagulate or ablate tissue, being able to produce a high enough local energy density to enable instant coagulation in regions of high perfusion, and by the availability of solid state devices that can be used to generate the required level of power (energy). A spot frequency of 14.5 GHz may offer a compromise between all of the factors listed above. Other appropriate spot frequencies that may be considered are 18 GHz, 20 GHz and 22 GHz.

To enable the antenna structures to be used within the human body, the materials used are preferably biocompatible and preferably do not present any risks to the patient. Materials identified for the antenna designs given here include: sapphire, silver, Teflon® and Parylene C.

The invention may not be limited to operation at a single frequency. For example, it may be desirable to operate the antenna over a frequency range of +/−50 MHz, around a spot frequency (e.g. 14.5 GHz). The dimensions of the antenna can be adjusted to accommodate any frequency (or range of frequencies) where the underlying theory related to the current invention remains valid. For some antenna arrangements it may be preferable to operate at a fixed frequency that lies within the frequency range of between 15 GHz and 25 GHz, where a uniform field can be generated along the edge of the blade of a small surgical antenna, for example, a scalpel blade, and the power loss along the feed cable between the bench top generator and the input to the surgical antenna is not excessive, for example less than 1.5 dB per meter. For devices operating at the upper end of the frequency range considered as being useful for implementation of the current invention (as defined above), it may be advantageous to move the microwave power generating devices to be in close proximity with the radiating antennas in order to minimise the effects of insertion loss within the energy delivery cable inserted between said power generating devices and said radiating antennas.

The materials disclosed for use in the current invention may be used for similar surgical treatment and/or measurement antenna structures that are optimised to operate at other microwave frequencies. In this instance, the geometry of the structure may be adjusted in accordance with the particular frequency of choice. Preferably, electromagnetic field simulation tools will be used to optimise the antenna structures.

Where the antenna structures are used with the dynamic impedance matching system described in WO2004/047659 it is desirable for the insertion loss of the cable assembly between the output of the control electronics (the generator) and the radiating antenna to be as low as possible, for example less than 1 dB, in order to ensure that the power available at the radiating antenna blade is maximised and also to enable a resonant cavity to be set-up between the output of the generator and the radiating antenna to allow for maximum power to be delivered even when large impedance mismatches between the radiating antenna and the tissue load are present. In order to achieve the required minimal insertion loss it may be preferable to use a waveguide cable assembly rather than a co-axial cable assembly. It is preferable to use a flexible waveguide cable assembly and it may be more preferable to use a flexible-twistable waveguide cable assembly.

Preferably, a customised waveguide flange system is used to connect the proximal end of the waveguide assembly to the output power delivery port of the generator. The customised flange system may include a spring slip arrangement or two circular threaded sections may be attached to the two waveguide flanges to enable the two flanges to be connected together. An advantage of these arrangements is avoiding the need to screw the two flanges together prior to commencing the treatment and then unscrewing them at the end of the treatment using conventional fixings. Conventional waveguide fixings do not lend themselves well to being used with a disposable unit due to the fact that four screws and associated nuts/washers are needed. The process of connecting and removing the treatment antenna assembly in this manner may be cumbersome for a surgeon or clinician (i.e. an operator) and so the alternative arrangement described above may overcome this potential limitation.

In one embodiment, the antenna comprises a loaded waveguide cavity, where the loading includes a piece of dielectric material. The dielectric material is preferably a low loss material, e.g. having tan δ or dissipation factor of less than 0.001 at the operation frequency. The dielectric material is preferably a hard material that is capable of being sharpened to produce a cutting blade or cutting edge that can be used to cut through biological tissue in a similar manner to that of a carving knife or a scalpel blade. Preferably, the dielectric material is biocompatible to enable it to be used directly in contact with biological tissue structures.

The waveguide section is preferably adapted to hold or clamp the dielectric material in place. The surface of the dielectric material may be roughened or knurled to provide a physical key to prevent the dielectric material from coming out of the waveguide section.

The choice of dielectric constant for the dielectric material may depend on the load impedance of the material that the dielectric material will be making contact with, i.e. the permittivity of the biological material. For example, a dielectric material with a relative permittivity of 5.2 may be used to provide an impedance match between an unloaded waveguide cavity and a block of biological tissue with a relative permittivity of 27. This analysis may not account for the dissipation factor associated with the materials, hence actual value of the permittivity may be modified according to the complex permittivity of the materials (electromagnetic field simulation can be used to optimise the structures).

Preferably, the electrical length of the dielectric material inside the waveguide cavity is an odd multiple of a quarter of the wavelength at the desired operating frequency to enable the material to act as an impedance matching transformer to match the impedance of the unloaded waveguide to the impedance of the biological tissue load.

Preferably, a section of dielectric material that protrudes from the waveguide into free space is tapered towards the cutting edge in order to minimise discontinuities by eliminating a large step in dielectric constant. This transformation may be implemented using a quasi-tapered rod that has a plurality of discrete steps that are preferably of length equal to a quarter of the wavelength at the frequency of interest or an odd multiple thereof.

Preferably, a tuning arrangement (e.g. a tuning filter) may be included in a waveguide cavity formed between a flexible cable assembly that provides power to the antenna and the dielectric material of the antenna. The tuning arrangement may take the form of one, two or three tuning screws (or stubs) that can be screwed into the waveguide cavity to introduce a capacitive or inductive reactance; the particular type of reactance and the value of the reactance will depend on the distance of the tuning screw inside the waveguide cavity. In the instance where more than one tuning screw is used, the distance between the centres of the screws is preferably an odd multiple of a quarter or an eighth of the guide wavelength. The tuning arrangement may enable the antenna to be statically impedance matched with various tissue load impedances representing various types of biological tissue that may be presented to the radiating dielectric blade.

Preferably, the antenna is statically impedance matched with the initial state of the biological tissue in order for the standing waves set up inside the waveguide cavity and the flexible cable assembly to be minimised. This is desirable even when the antenna is used in conjunction with a dynamic impedance matching system. This condition offers advantage in terms of minimising heating of the waveguide cavity and the flexible cable assembly, and preventing material stresses and/or breakdown due to high voltages or currents generated due to the standing waves set-up inside the structure.

The static impedance match may be achieved using permanent posts or stubs that reside inside the waveguide cavity.

Preferably, the surfaces of the waveguide are coated with a material that has a high conductivity in order to minimise conductor losses. Silver may be used. It may also be desirable to coat a section of the dielectric material that protrudes outside the waveguide cavity into free space with a metallic material in order to prevent surfaces of the dielectric material that are not in contact with the biological tissue from radiating into the free space. An advantage of coating the surface of the dielectric material with a layer of silver material is that it has been shown that long term toxicity will not effect the structure and that silver is an effective anti-biotic, hence it may be desirable for a portion of the non-radiating section of the dielectric blade to be in contact with the biological tissue. It should be noted that the dielectric blade may be coated with a metallic material where only the portion of the material that forms the radiating blade, or the portion required to make contact with the biological tissue, is left exposed. This arrangement ensures that only the biological tissue is exposed to microwave radiation.

As mentioned previously, the advantage of using high frequency microwave (or non-ionising) radiation is that the depth of penetration is limited hence the risk of exposure is also limited. The risk of radiating into free space is further reduced by the fact that the antenna structures introduced in this work have been designed to match well into biological tissue, but to be poorly matched into the impedance of air, i.e. 377Ω. The risk of radiating energy into free-space is even further reduced by the fact that the sensing electronics associated with the system used to generate and deliver the treatment energy may sense that the antenna is radiating into free space and can automatically reduce the output power to near zero, i.e. 1 mW to 10 mW.

In another embodiment, the antenna comprises radiating microstrip patches (or microstrip antenna structures) fabricated onto the cutting edge of a blade or knife structure. In this arrangement it may be preferable for the patch antennas and the feed structure to be plated or etched onto the surface of a hard microwave ceramic material where said ceramic forms the microwave substrate for the microstrip transmission lines that form the feed structure. The microstrip patches may be fabricated along the edge of the blade section of the ceramic material. The microstrip patch antennas may be set-up to radiate along the edge of the blade. It may be preferable for one side of the ceramic material to be metallised over the complete surface to provide a ground plane or return path for the feed structure and the radiating patch antennas. The patch antennas may be set up to radiate along the edge of the patch that is physically opposite to the input feed line.

Strip-line (or tri-plate line) structures may be used to form the feed network in order to prevent the feed lines from radiating into free space. In this arrangement, the microstrip lines may be fabricated onto the first face of a first dielectric substrate (e.g. a hard ceramic) and for the second face to be entirely metallised. The first face of a second substrate (normally the same material as the first substrate with the same relative permittivity) is then placed on top of the first face of the first substrate material containing the microstrip feed lines to form a sandwich, and the second face of the second substrate is also entirely metallised. This structure is known as a strip-line structure and provides an enclosed environment for the electromagnetic waves to propagate and also provides a shield to eliminate the risk of radiation coming off of the feed lines and propagating into free-space. If the thickness of the two substrate materials is identical then the width of the microstrip lines will be approximately half of what they are in the case of the single sided open microstrip feed structure.

The feed line structure may be implemented in the form of a corporate fed structure or a structure comprising of fixed impedance feed lines (e.g. 50Ω) and quarter wave transformers. Other feed line structures that can be used to feed a plurality of radiating patch antennas will be known to a person experienced in the art of microwave engineering, and these structures may also be used.

The patch antenna structure may be fabricated onto a scalpel blade which has a layer of dielectric material (the substrate) attached to it, where the first side of said dielectric material covers the complete surface of the scalpel blade. The second side of the substrate material is then metallised by, for example, evaporating a layer of metal onto the surface or using silver paint. Areas or zones of said metallisation layer can then be etched away to leave the microwave feed structure and the radiating patch antennas. A second substrate layer with a ground plane on one side may be used to form a strip-line structure to prevent the feed lines from radiating into free-space (this type of structure has already been described above).

A spray-on dielectric material may be used to coat one side of the scalpel blade. Since the thickness of the dielectric material governs the impedance of the microstrip lines, it is desirable for the thickness of the dielectric material to be constant over the entire surface of the scalpel blade to ensure that feed lines and the radiating patches are of a controlled impedance otherwise mismatches and reflections will occur, which may lead to a structure that radiates inefficiently or heats up.

A further structure that may be considered is a co-axial feed cable with a single 'H'-loop radiating antenna attached to the distal end to provide the microwave energy required for blood sealing. Said 'H'-loop antenna may be connected to a scalpel blade or another structure that provides a sharp cutting edge to enable the desired cutting/sealing action to take place. The 'H'-field loop may be located at the centre of the blade, and for the section of blade where the loop is placed may be removed to enable the radiating fields to propagate around the blade. Preferably, the blade has a shape of a scalpel blade and is made from a hard ceramic material that lends itself to be sharpened to provide an effective mechanical cutting edge.

Other structures that may be considered include co-axial monopole and co-axial dipole radiating structures connected to a suitable cutting device. Again, monopole/dipole structures may be located inside a cutting blade arrangement.

Yet another structure may consist of a plurality of said co-axial monopole/dipole structures, fed using a co-axial impedance matching transformer connected to a co-axial cable, where said co-axial monopole/dipole radiators are mounted onto a cutting device, such as a scalpel blade, and arranged to efficiently radiate energy into the tissue whilst the blade cuts through the tissue.

Yet another structure may be a device similar in physical form to that of a 'paint stripper' or a 'chisel' with a plurality of radiating patch antennas deposited onto the edge of the blade section to enable the blade to be pushed through the tissue to separate the tissue into two sections with the microwave energy radiating into the tissue during the cutting process to seal off blood flow.

It is desirable for the antenna to include a radiating cutting blade that is adapted effectively to radiate microwave energy into tissue and not into free-space. The may be achieved using various blade profiles including 'tooth' shapes, hemispherical shapes and scalpel blade shapes. For example, a triangular structure with a 60° angle at each of the base corners may be considered to provide the ability to "dig" into the tissue.

Feed structures that may be suitable for use in the invention can be broadly divided into two sections. The first is waveguide power splitters and the second is microstrip (or strip-line) power splitters. In one embodiment, a microstrip splitter is used to feed four waveguide sections, hence this arrangement may be considered as being a combination of the two techniques. In another embodiment, a Hybrid ring is used to split the power generated by the microwave source into two equal parts. The two outputs are then used to feed two waveguide assemblies each containing a 13 mm sapphire blade to give a radiating edge that has an overall length of approximately 26 mm.

Corporate feed line structures or quarter wavelength feed structures may be used, where all the feed lines are of fixed impedance.

Suitable waveguide splitters may include: Hybrid ring (or rat race) couplers, resonant cavity splitters and hybrid 'T' configurations. Suitable microstrip power splitters may include: Wilkinson couplers, corporate feed networks, quarter wave power splitters, non-resonant splitters and 3 dB couplers.

The antenna may have a long radiating blade, for example a blade having a length of 68 mm or greater. A plurality of individual blades may be combined together to produce a single blade that can produce even or uniform tissue effects along the length of the blade.

The microwave surgical antenna of the invention may be used for tumour ablation of large volume solid tumours within a biological system. Specific antenna structures that are appropriate for this function include loaded waveguide structures which incorporate a means of adjusting the impedance match between the radiating apertures and the cancerous tissue, and co-axial structures that comprise of either a large diameter co-axial cable with a radiating cone, or a plurality of radiating monopoles fed using a co-axial impedance matching transformer.

In one embodiment, a Hybrid ring is used to split the energy produced by a source. The two output ports from the Hybrid ring device are used to feed two individual waveguide cavities that contain a sapphire blade. If the wall thickness between the two separate sections is limited to around 1 mm, then it may be possible to produce a uniform field along a blade length that is equal to the length of two individual sapphire blades. In theory, the wall thickness between the two blades may only need to be equal to several skin depths where the microwave energy flows. At 14.5 GHz, the skin depth in copper or silver is around 2.5 µm. Given that the 99% of the microwave energy flows in a thickness equal to five skin depths, it is feasible to make the wall between the two blades around 25 µm in thickness, which will have a negligible impact on the fields generated inside the individual waveguide structures, but will provide a quasi-continuous field along a blade length equal to two individual sections placed side by side or adjacent to one another. In this arrangement, the remaining walls may provide the mechanical support necessary to hold the radiating blade in position. Also, a key may be provided on the surface of the blades to ensure that the blade remains in position and cannot be pushed into the waveguide cavity or fall out of the waveguide cavity. A means of static tuning may also be included in each of the two waveguide sections to enable the radiating blade to be statically impedance matched to the impedance of the biological tissue under investigation.

The length of the radiating blade may be further increased using a microstrip feed structure to split the energy generated from the source into four equal parts and then use the four outputs to drive four radiating blades contained inside a waveguide cavity. In one embodiment, each waveguide section is fed using a 'H'-loop feed, which may be a loop of wire that is either a half wavelength in length at the frequency of operation or a multiple thereof. It is preferable for one end of the 'H'-loop to be connected to the microstrip line and for the other end to be connected to one of the walls of the waveguide, which is also attached to the ground plane of the microstrip feed line structure.

A Rogers 5880 dielectric material may be used to provide the substrate for the microstrip feed line structure, where the thickness of the substrate material, the ground plane metallization, and the microstrip feed lines are selected to be capable of handling the power level at the input feed connector.

Preferably, the feed line structure is enclosed to prevent radiation from the microstrip feed lines coupling into free space. This can be achieved by placing a metal can over the feed line structure, where the dimensions are such that moding cannot occur within the structure. The microstrip feed line structure may be implemented using a strip-line structure, where a second substrate material is placed on top of the feed lines and the second side of the second substrate material is metallised over its entire surface.

Other arrangements used to extend the length of the radiating blade include using radiating microstrip structures fabricated along the edge of cutting devices, for example, scissors, scalpels, chisels, paint strippers, Stanley® knives and various other knife structures or instruments. In order to provide a uniform field along the length of the blades, it is preferable for a plurality of microstrip structures, for example, square or rectangular patch antennas, slotted radiators or travelling wave antennas, to be fabricated along the length of the blade.

Alternatively or additionally, the antenna comprises one or more radiating dielectric rods. The rods may be pointed to enable the antenna to be pushed inside the tumour to cause effective ablation of cancerous tissue as the antenna structure is pushed into the tissue.

Thus, in a third aspect, the invention may provide an ablation probe comprising a elongate body having an insertion end adapted to penetrate tissue; a plurality of radiating elements at the insertion end, each radiating element being adapted to emit a microwave radiation field for ablating tissue; and a feed structure connectable to a microwave power source and arranged to transport microwave power to the radiating elements; wherein the feed structure is arranged to split the microwave power substantially evenly between the radiating elements whereby the emitted radiation field is substantially uniform at the insertion end. Such a probe may be particularly suitable for treating solid tumours in large organs. The probe may be equipped with a cutting arrangement according to the first aspect in order to enable access to the treatment site. The elongate body may comprise a catheter arranged to carry a plurality of antennas, which protrude from the insertion end. The radiating elements may be co-axial monopole antennas.

Arrangements using a plurality of co-axial radiating elements may be used to treat large solid tumours. These arrangements may comprise of a plurality of monopole co-axial radiating elements fed from a large diameter rigid co-axial cable, for example, six 2.2 mm diameter radiators fed from a 12 mm co-axial cable. These arrangements may require an impedance matching transformer to transform the impedance of the co-axial feed cable to the impedance given by the parallel combination of smaller diameter co-axial cables connected at the feed point (star point). The impedance seen at the feed point may be influenced by the impedance seen at the distal end of each of the co-axial lines, i.e. the end that makes contact with the biological tissue load.

A microstrip structure may be used to fabricate the feed line and the impedance transformer, where a plurality of small diameter, for example 1 mm to 2 mm, co-axial sections with radiating elements connected to the distal end are attached to said impedance transformer.

The co-axial radiators may be adapted to fit inside a cone structure in such a manner that they produce a uniform field pattern over the surface of the cone. The cone may be made from a hard low loss microwave ceramic material that is attached to the feed structure. The cone shape structure may be pointed to enable the antenna to be pushed inside the tumour to cause effective ablation of cancerous tissue as the antenna is pushed into the tissue structure. In this arrangement the radiating cone may assist in enabling the antenna to be pushed through the tumour. A blade arrangement may be attached to the cone to enable an incision to be made prior to the antenna being pushed through the biological tissue to cause tumour ablation.

The geometry and choice of materials used in the antenna design can be optimised using electromagnetic field simulation tools, for example, Computer Simulation Technology (CST) Microwave Studio®.

The surgical antenna and the cable assembly may form a single use item that is sterilised and comes in a sterile package. The proximal end of the cable assembly can be attached to a bench top generator using a connector assembly that enables ease of attachment. A snap-on connector or a customised push-fit arrangement may be used.

The radiating structures discussed herein may be calibrated at their distal tip (or the radiating blade) to enable them to be used with the treatment and measurement system disclosed in WO 2004/047659 or WO 2005/115235. The ability to calibrate the antenna structures can enable energy delivery into tissue to prevent blood loss to be optimised in terms of being able to deliver the demanded power level into the tissue even when the radiating blade is not well matched with the tissue load. The ability to deliver energy in this manner, coupled with the aforementioned advantages associated with using high microwave frequencies may offer significant advantage over other existing lower frequency technologies.

BRIEF DESCRIPTION OF THE DRAWINGS

A detailed description of embodiments of the invention is given below with reference to the accompanying drawings, in which.

DETAILED DESCRIPTION; FURTHER OPTIONS AND PREFERENCES

The operation of the resection antennas described here may be described as being similar to that of a butter knife or meat knife. Various blade structures have been considered for the implementation of the current invention, namely: a 'tooth' shape blade, a scalpel shape blade, a 'paint stripper' shape blade, a chisel shape blade, a hemispherical shape blade, a kitchen knife shape blade and a carving knife shape blade. In the instance where a 'tooth' shape blade is used, it may be preferable for the tooth to take the form of a triangular structure with a 60° angle at each of the base corners to provide the ability to "dig" into the tissue.

Figure 1:
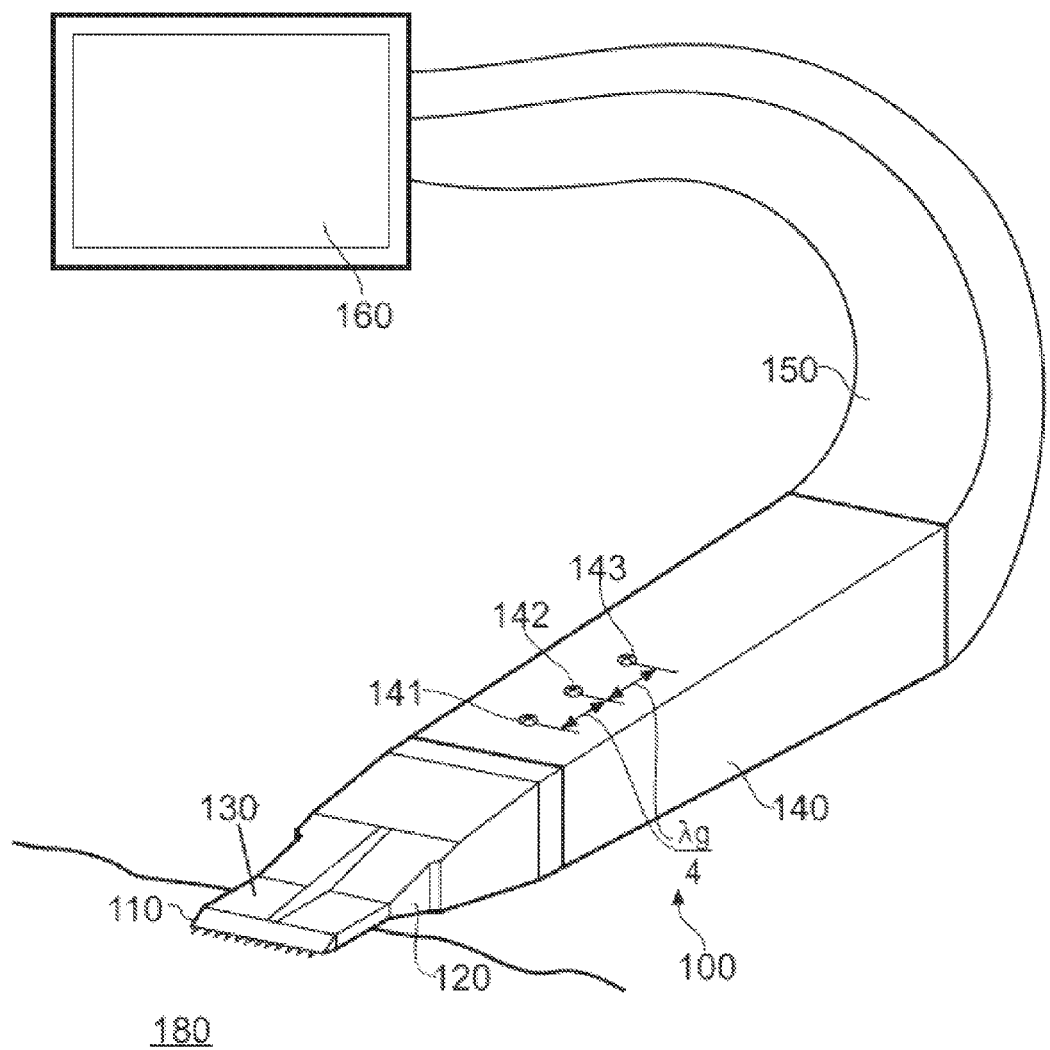
FIG. 1 shows a tunable liver resection antenna that is an embodiment of the invention.

FIG. 1 shows a surgical antenna structure 100 for resection applications. The arrangement shown here is a loaded waveguide antenna, which uses a sapphire material to form the radiating section or blade 110 and, in this particular instance, also act as a sharp cutting tool. The shape of the sapphire section inside the waveguide and the design of the end section or blade housing provide a good impedance match between the biological tissue 180, the sapphire blade 110 and the waveguide cavity 140. The overall structure consists of the sapphire blade 110, a rigid section of waveguide 130, a waveguide adaptor or flange 120, a length of fixed waveguide cavity 140, three tuning stubs 141, 142, 143 and a cable assembly 150. The cable assembly 150 can be a flexible or flexible/twistable waveguide section or a co-axial cable with an appropriate adaptor to convert between a waveguide system and a co-axial system. The sapphire section 110 is partially metallised over its surface using an electroforming process with only the end of the blade exposed, i.e. the radiating section. The sapphire material provides an impedance match between the impedance of the unloaded waveguide section 120, which is a high impedance close to that of air, and the biological tissue, which may be a low impedance, for example, between 100Ω and 1Ω. The size of the fixed waveguide 140 depends on the frequency of operation. In the arrangement shown in FIG. 1, a section of WG18 (WR62) flexible waveguide was used that operates over the frequency range of between 12.4 GHz and 18 GHz. This is a suitable structure to use at the preferred frequency of operation discussed herein, 14.5 GHz.

Tuning stubs 141, 142, 143 are used to enable the static impedance match between the biological tissue 180 and the antenna assembly 100 to be optimised. In the arrangement shown in FIG. 1, the spacing between the three tuning screws was a quarter of the guide wavelength, where the guide is defined here as being WR62. Three tuning screws arranged in this manner enable an impedance match between the tissue load 180 and the antenna 100 to be obtained where the tissue load may take any value of impedance on the Smith chart. The tuning stubs may be small posts inserted inside the waveguide cavity 140. The tuning screws can be replaced with fixed posts in a manufactured device.

Waveguide section 120 holds the sapphire blade in position and acts as an interface between second waveguide section 140 and the sapphire material 110. FIG. 1 shows the sapphire blade in contact with a block of biological tissue 180, e.g. liver.

The device may be used with the dynamic impedance matching system described in WO 2004/047659 to enable the demanded power to be delivered into variable tissue load impedances, for example, liver and blood. This may overcome problems associated with other systems where energy delivery into tissue ceases if the antenna becomes mismatched with the load impedance presented by the tissue. By calibrating the antenna it is possible to effectively connect the output impedance of the antenna to the impedance of the biological tissue that forms the system load.

The radiating section of the surgical antenna may be coated with a thin layer, for example, 10 µm, of material that will prevent the radiating tip from adhering to the tissue once the microwave energy has coagulated the tissue and enable the device to be biocompatible. Coagulated blood may otherwise stick to the radiating blade. Suitable materials that may be used include Teflon® and Parylene C.

Other shapes can be used for the radiating blade. For example, a 'tooth' shape radiating structure may be used, or the shape of the cutting edge and the radiating section may resemble a conventional scalpel blade. Electromagnetic field simulations and optimisation are performed on each blade shape (or structure) and adjustments are made to the structure of the waveguide housing 120, 130, the position of tuning stubs 141, 142, 143, and the shape of the dielectric material (sapphire or other hard ceramic material) 110 that protrudes inside and outside the waveguide cavity in order to optimise the structure.

The dielectric material inside the waveguide cavity 120, 130 is tapered in order to maximise the field coupled into the radiating dielectric. Alternatively or additionally a plurality of dielectric materials or a single material that exhibits a plurality of dielectric constants can be used. The advantage of using a tapered section to match the impedance of the waveguide to the impedance of the biological tissue is that the step between the guide impedance and that of the tissue is not so abrupt, hence the discontinuities associated with the transformation are minimised. Tapering may take place over an electrical length equal to several wavelengths at the frequency of interest, i.e. effectively, a plurality of quarter wave transformations take place.

In the arrangement shown in FIG. 1 only one transformation was used to transform the impedance of the unloaded waveguide to the impedance of the biological tissue. For example, if the dielectric constant of the tissue to be treated is approximately 40 at the frequency of operation, then a material with an electrical length of $(2n-1)\lambda/4$ (where n is an integer), and a relative permittivity of $\sqrt{40}=6.32$ (assuming the waveguide sections 120, 130, 140 are unloaded) is required to achieve an impedance matched structure. In this approximation all materials are assumed to be lossless, i.e. their dissipation factor or $\tan \delta$ is zero.

As an alternative to the rectangular waveguide (FIG. 1), a cylindrical waveguide, square waveguide, or a more esoteric shape guide that accommodates the specific user requirements can be used.

In the specific embodiment shown in FIG. 1, the width of the sapphire blade, or the cutting edge, is 13 mm. The blade design is optimised for an operating frequency of 14.5 GHz where the physical profile or cavity dimensions of waveguide WG18 (WR62) is matched to the radiating sapphire blade. The impedance match at the transition is simulated to be better than −25 dB return loss over the frequency range of between 14.25 GHz and 14.75 GHz when using the model for a block of liver obtained from http://niremf.ifac.cnr.it/tissprop/, where the relative permittivity is given as 27.222 and the conductivity is given as 14.448 S/m at a spot frequency of 14.5 GHz. Ridges are included on waveguide section or transition 120 in order to reduce the voltage variation across the waveguide aperture. The radiating sapphire blade 110 is soldered to a transition from WG18 to WG17 120. The wall of the sapphire radiating blade 110, is electroformed. A physical key is introduced into the blade to ensure that it is held tightly in position inside the waveguide and cannot fall out or become accidentally detached.

Specific materials suitable for the antenna structures disclosed herein are:

(a) for the radiating/cutting blade and matching transformer:
Sapphire ($AL_2O_3$) with a hardness of 1900 Knoop (9 Moh), dielectric constant perpendicular to C axis=9.3, dielectric constant parallel to C axis=11.5, and loss tangent (or dissipation factor or $1/\Omega$)=0.00005,
A particular microwave ceramic material from Morgan Electroceramics known as D6, which has a dielectric constant=6.5+/−0.5 and loss tangent=0.002, and can be used over the frequency range of between 3 GHz and 20 GHz;

(b) for the coating material:
Parylene C, Teflon or PTFE may be used to coat the radiating/cutting blade and/or to coat the overall antenna structure, as they are biocompatible and low loss at the frequency of interest. Dielectric heating loss may be circumvented by using a very thin layer of said materials, for example 10 µm to 100 µm;

(c) for the blade housing, waveguide section and cable assembly:
Brass, aluminium, copper or silver, which have high conductivity thereby minimising conductor losses in the waveguide and limiting heating of the waveguide structure caused by conductor losses. For example, a silver plated aluminium structure can be used, where the plating thickness is several skin depths at the frequency of interest to ensure that the majority of the microwave energy is contained within this depth.

Figure 2:
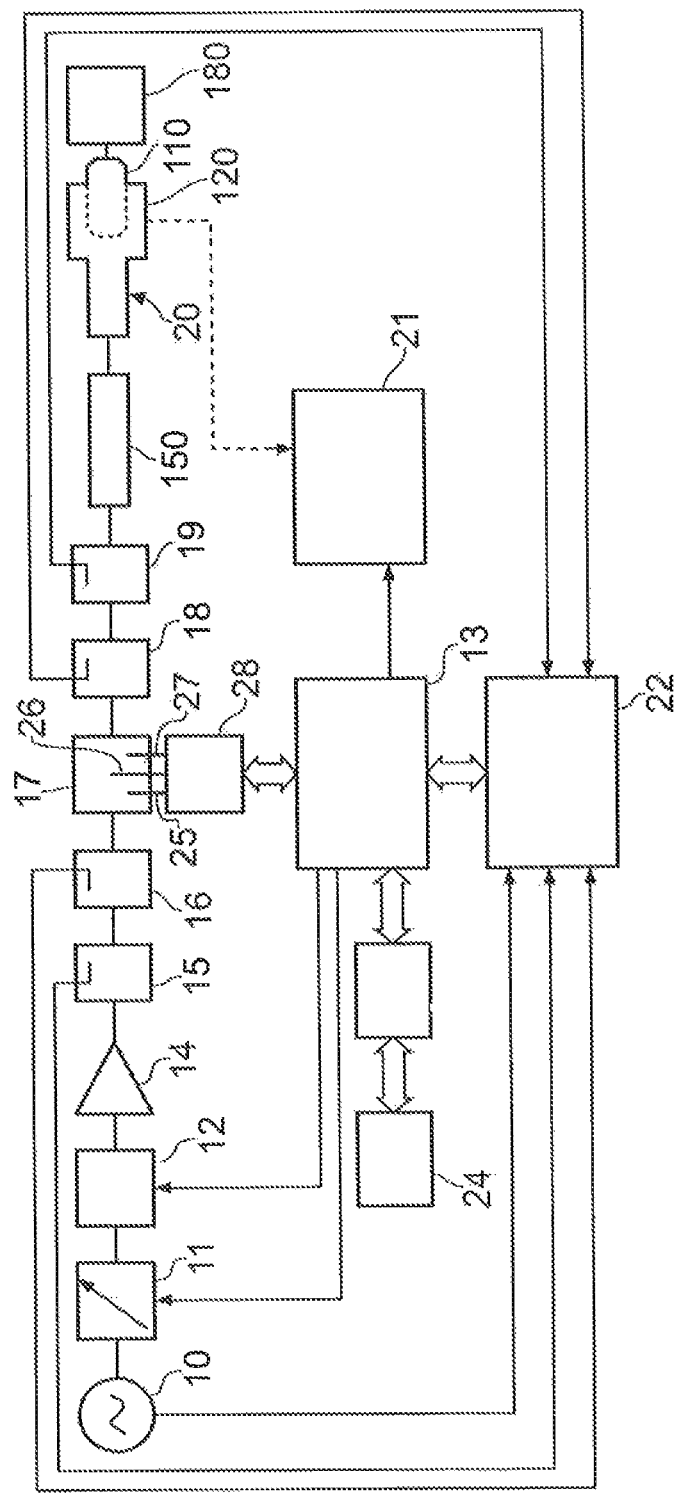
FIG. 2 shows a schematic system diagram for a dynamic impedance matching treatment system which incorporates the antenna of the invention.

FIG. 2 shows the radiating antenna structure 20 of FIG. 1 used with an automated impedance matching system to enable efficient delivery of energy into biological tissue 180 under the condition of a changing or dynamic load impedance, for example, the impedance of blood, the impedance of the surface of the liver, or the impedance of a tumour contained within the liver. Specific details of the system shown in block diagram format in FIG. 2 can be found in WO 2004/047659, but a brief summary of the operation of the system is included here. The dynamic impedance matching system shown here uses a source oscillator unit 10, which produces a low power signal at the system frequency of 14.5 GHz. Source oscillator 10 may also produce a second signal that is used to provide the local oscillator signal for microwave receiver unit 22. The microwave receiver unit 22 is a heterodyne receiver to enable both magnitude and phase information to be extracted from the signals provided by the coupled ports of forward and reflected power directional couplers 15, 16, 18, 19. In this embodiment, a local oscillator signal is generated at a microwave frequency of 14.45 GHz, to provide a first intermediate frequency (IF) of 50 MHz. FIG. 2 shows the RF output from the source oscillator unit connected to power level controller 11, which is used to control the level of power delivered into tissue load 180. The level is set using a signal provided by digital signal processor 13. This signal is based on information provided to user interface 24 via the user or operator. The output from power level controller 11 is connected to modulation switch 12, which is used to control the format of the output power delivered into tissue load 180, i.e. pulse width, and duty cycle. The switch position is set using a signal provided by digital signal processor 13, which is based on information provided to user interface 24 via the user. The output signal from modulation switch 12 is amplified using amplifier block 14 to provide a power level that can be used to effectively ablate biological tissue. The amplifier block may be a solid state (e.g. GaAs) power amplifier or, for higher power outputs, a travelling wave tube. The output from power amplifier 14 is connected to the input of first forward power coupler 15, which is configured to measure a portion of the power produced at the output of power amplifier 14. The output from first forward power coupler 15 is connected to first reflected power coupler 16, which is configured to measure a portion of the reflected power produced at the input to adjustable tuning filter 17. The tuning filter 17 acts as an impedance adjuster, where the impedance of the unit can be adjusted to any impedance to enable the impedance 'seen' by the radiating section of surgical antenna 20 to be impedance matched with the load impedance created by biological tissue 180. The output from tuning filter 17 is connected to the input of second forward power coupler 18, which is configured to measure a portion of the power coming out of tuning filter 17. The output from second forward power coupler 18 is connected to the input of second reflected power coupler 19, which is configured to measure a portion of the reflected coming back along cable assembly 150 due to an impedance mismatch between the output radiating blade 110 of antenna 20 and biological tissue load 180. The measured signals from the coupled ports of forward power couplers 15, 18 and reflected power couplers 16, 19 are fed into microwave receiver unit 22, which converts the signal to a lower frequency that can be used by an analogue to digital converter (ADC) contained within signal processor unit 13 that is used to extract phase and magnitude information used to calculate the required adjustments to the tuning elements of tuning filter 17 to enable the energy produced at the output of power amplifier 14 to be impedance matched with the tissue load 180 seen at the radiating tip of surgical antenna 20, thus enabling the system to deliver the demanded power level into a variable impedance load. In this embodiment, the tuning elements are three tuning rods (or stubs) 25, 26, 27 that are physically (mechanically) moved in and out of a waveguide cavity to enable the output power from power amplifier 14 to be delivered into a load presented to the radiating section of surgical antenna 20 by biological tissue 180. Power varactor diodes or power PIN diodes can also be used as the tuning elements. Tuning stubs 25, 26, 27 each provide a capacitive or inductive reactance, and the value of this reactance is a function of the distance of the particular tuning rod inside the waveguide cavity. The centres of adjacent tuning stubs are separated by either a quarter or an eighth of the guide wavelength for the specific waveguide used at the frequency of operation. The position of the tuning stubs inside the waveguide cavity is determined by the signals at the input of stub/tuning element controller 28, which, in this instance, is an electromechanical actuator. The input signals used to control stub/tuning element controller 28 are provided by digital signal processor 13, and these signals are based on the signals from microwave receiver unit 22, which are themselves based on the information measured at the coupled ports of directional couplers 15, 16, 18, 19. The surgical antenna 20 is calibrated at the distal radiating blade 110 to enable the automatic impedance matching system described above to be used. Before use in a surgical procedure, the antenna 20 is inserted inside calibration unit 21 and a single port calibration is performed to enable the signal 'seen' at the distal end of antenna 20 (radiating sapphire blade) to be referenced to digital signal processor unit 13, where phase an magnitude information is extracted using digital signal processing methods. The calibration effectively removes the phase and magnitude changes caused by all components in the system between the distal tip of the radiating antenna (the aerial) and the input to the digital signal processor to enable the measured signal to be representative of the biological load that the distal tip of the radiating antenna makes contact with.

Figure 3:
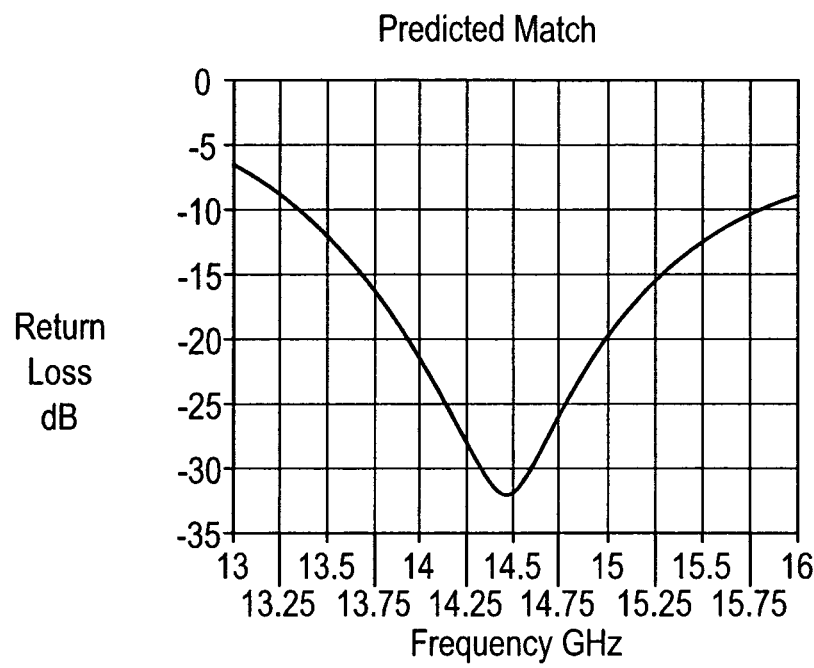
FIG. 3 shows a graph of modelled return loss for an antenna according to the invention in liver.

FIG. 3 shows a graph of the modelled return loss as a function of frequency for the sapphire blade shown in FIG. 1, where the blade 110 is inserted inside the block of liver 180, whose electrical characteristics are defined by tissue models given in: http://niremf.ifac.cnr.it/tissprop/. The response given in FIG. 3 indicates that the return loss at the frequency of interest of 14.5 GHz will be greater than −30 dB, which implies that the energy being delivered at the distal end of sapphire antenna structure is well matched with the impedance of the liver model and that the majority of the energy produced by the radiating structure will be delivered into the liver tissue.

Figure 4:
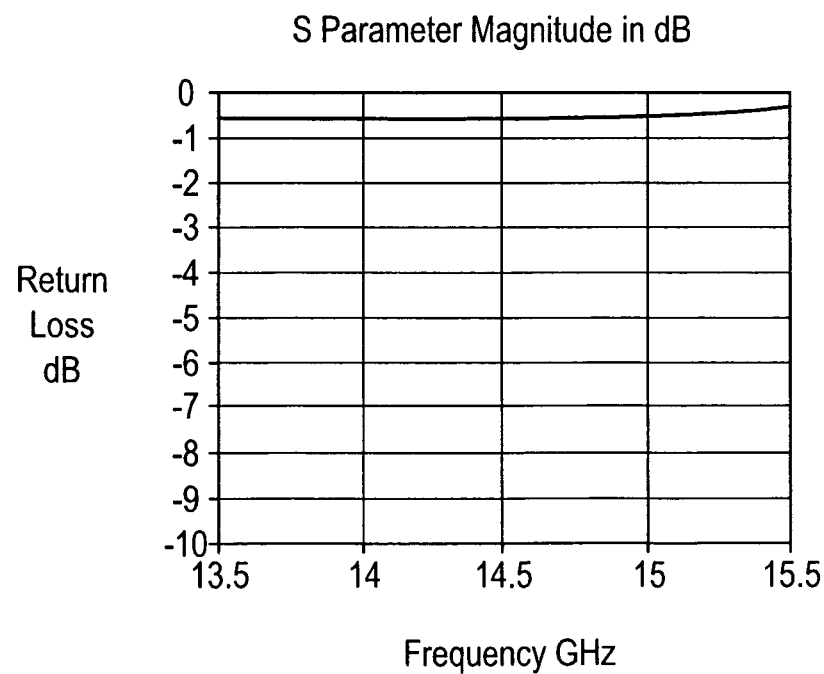
FIG. 4 shows a graph of modelled return loss for an antenna according to the invention in free space.

FIG. 4 shows a graph of the modelled return loss as a function of frequency for the sapphire antenna radiating into free space. This graph indicates that the return loss at 14.5 GHz will be less than −1 dB, which implies that most of the energy will be reflected back along the antenna structure towards the energy source where the device is radiating into free-space. The radiating antenna structure is optimised for this condition in order to minimise the amount of radiation transmitted into free space. When the antenna is used with the rest of the system, the reflected power level will be sensed and the source power level can be reduced to further minimise risk of radiating energy into free-space.

Figure 5:
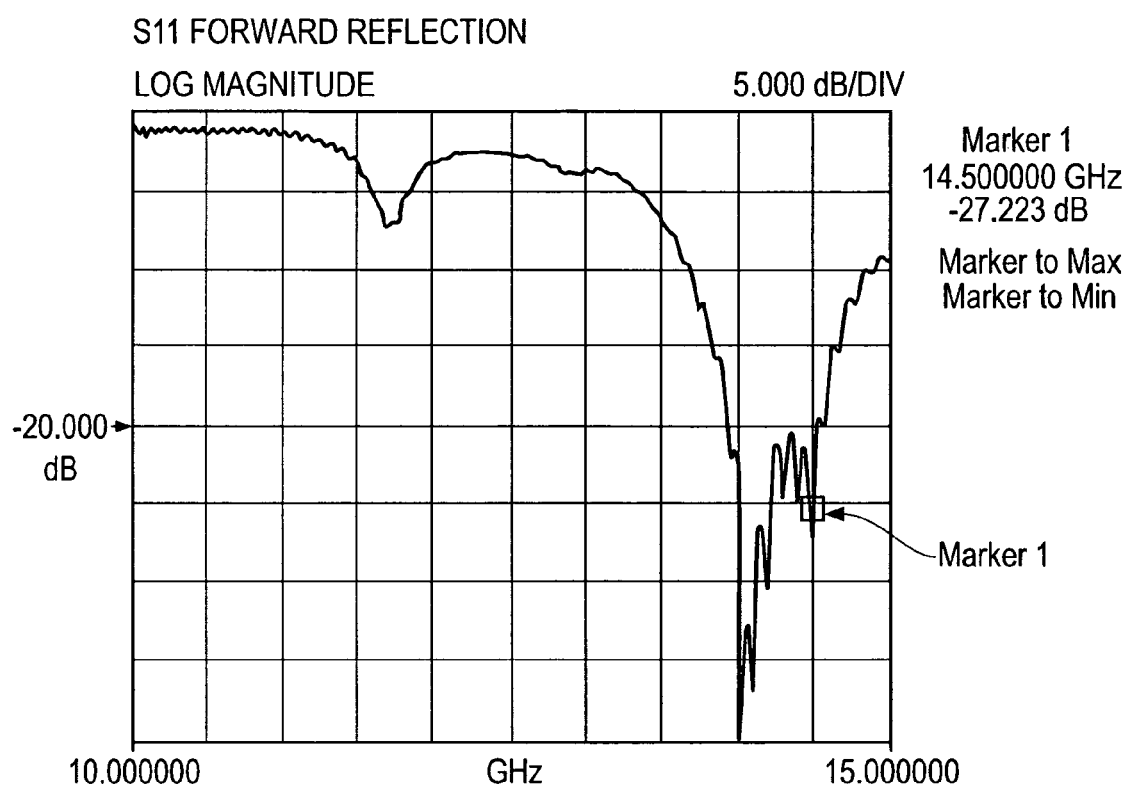
FIG. 5 shows a graph of actual return loss for an antenna according to the invention in liver.
Figure 6:
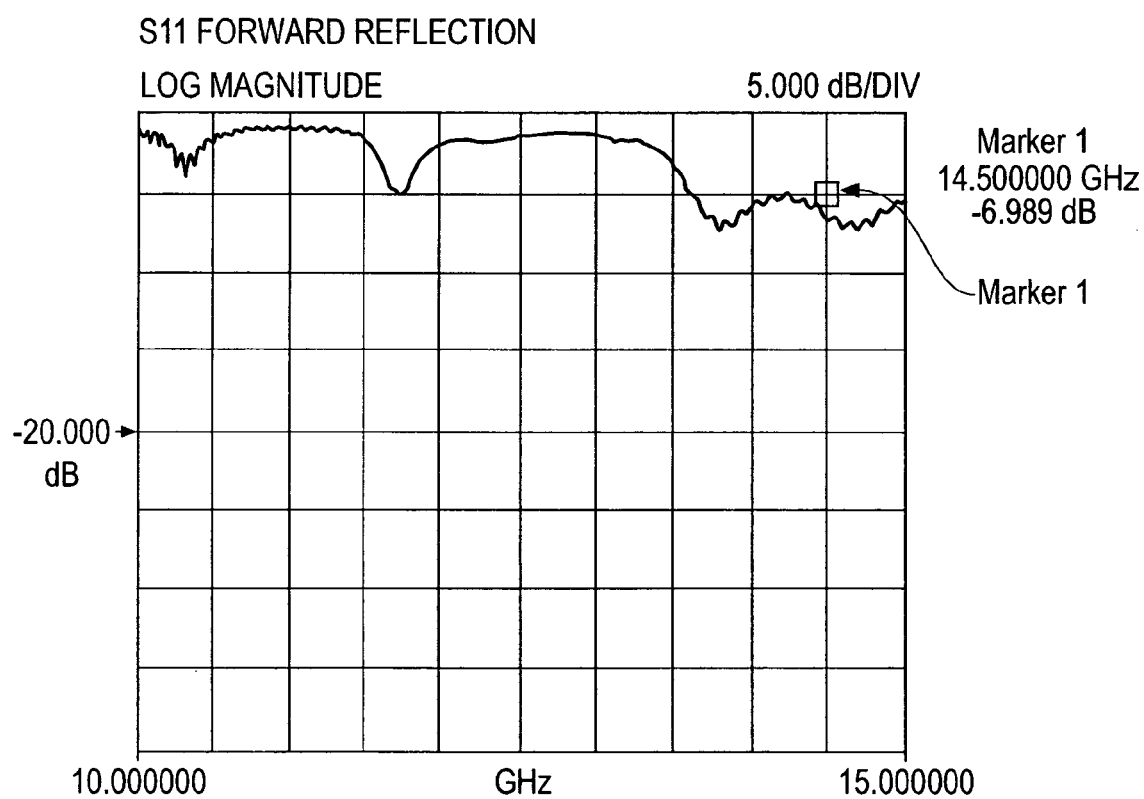
FIG. 6 shows a graph of actual return loss for an antenna according to the invention in free space.

FIG. 5 shows a plot of the measured return loss as a function of frequency over a frequency band of between 10 GHz and 15 GHz with the radiating section of the antenna (the sapphire blade) inserted into a piece of morbid porcine liver. The graph shows that the structure is well matched over the frequency band of between 14 GHz and 14.5 GHz. A marker placed at 14.5 GHz shows that the return loss at this frequency is −27.223 dB, which indicates that the antenna structure is well matched into a non-perfused porcine liver load at the frequency of interest for the current invention. FIG. 6 shows a plot of the measured return loss as a function of frequency over a frequency band of between 10 GHz and 15 GHz with the radiating section of the antenna radiating into free space. At 14.5 GHz the return loss is −6.989 dB.

The insertion loss at 14.5 GHz for 1.2 meters of flexible waveguide used for the cable assembly 150 in FIG. 1 between the generator and the radiating antenna is 0.621 dB. In terms of power loss: assuming that the power available at the output of the microwave generator is 50 dBm (100 W), then the power available at the input to the antenna structure will be: 50 dBm −0.621 dB=49.379 dBm=86.676 W. This implies that 13.32 Watts of power will be lost along a cable assembly of 1.2 meters in length, thus the loss per centimeter will be 0.111 W, which indicates that the delivery structure will not heat up even when the energy is applied continuously for a long period of time, for example, 10 minutes or longer. It is also desirable to minimise the insertion loss of 150 to enable a resonant cavity to be set-up between the output of power amplifier 14 and tissue load 180 to allow the dynamic matching system shown in FIG. 2 to work effectively to provide energy delivery into tissue even when the load and source are mismatched.

Figure 7:
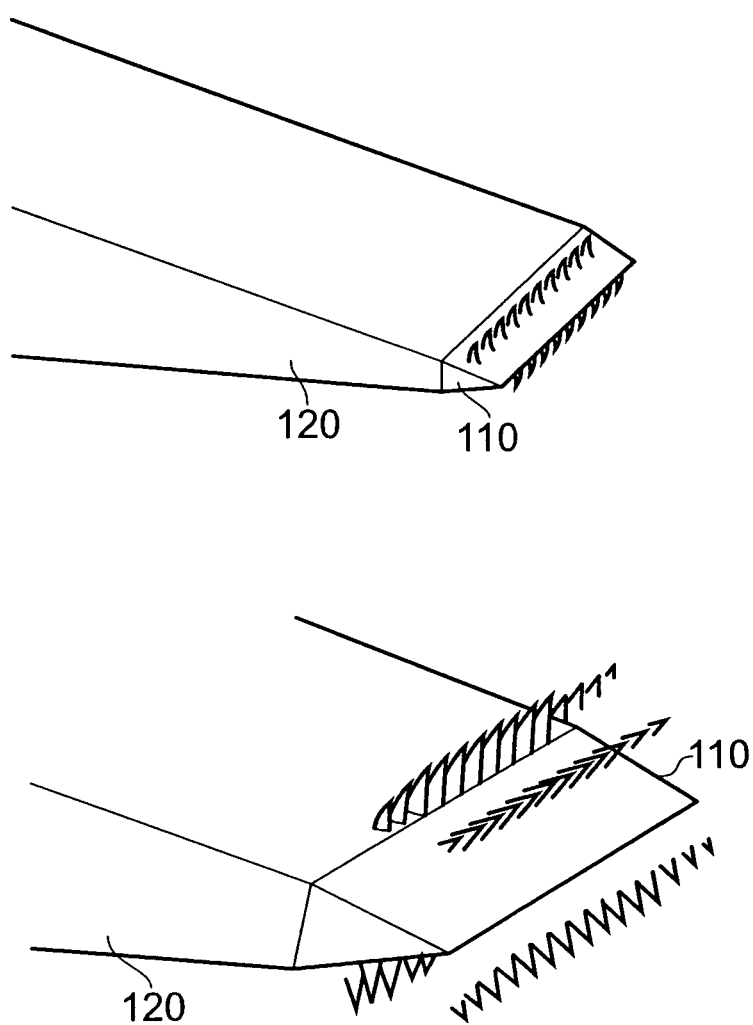
FIG. 7 shows the results of an electromagnetic field simulation on an antenna that is an embodiment of the invention.
Figure 8:
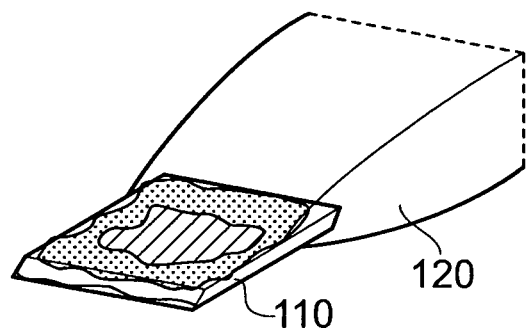
FIG. 8 shows the field distribution for the sapphire blade from the simulation of FIG. 7.
Figure 9:
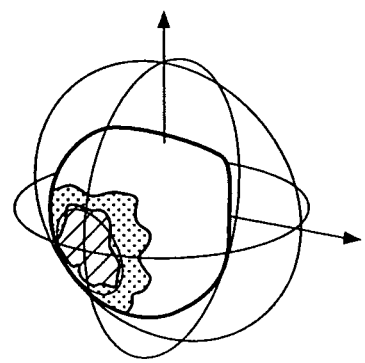
FIG. 9 shows the far field distribution for the antenna from the simulation of FIG. 7.

FIG. 7 shows the results from electromagnetic field simulations with the radiating sapphire blade immersed into a block of liver. The simulation was performed at a fixed frequency of 14.5 GHz. It can be seen that the maximum power flow is in the region of the blade and that the power density and the electric field is uniform along the surface of the blade. FIG. 8 shows the field distribution within the sapphire blade, where it can be seen that the electric field is maximum at the radiating end of the blade where said blade enters the biological tissue, and that the electric field generated along the length of the blade is uniform. FIG. 9 shows the far field pattern for the antenna. It can be seen that the antenna is directional and has a maximum gain of 11.19 dBi.

To separate a region of morbid porcine liver tissue 180 using the radiating sapphire blade antenna discussed above, the following conditions can be used:

1. Power level at the radiating blade: 60 W
2. Mode of operation: Continuous wave
3. Duration of operation: 45 seconds
4. Frequency and stability: 14.5 GHz (+/−1 kHz)
5. Initial temperature of liver: Approximately 15° C.

In this case, the depth of penetration is limited to the depth of penetration by radiation.

Figure 10:
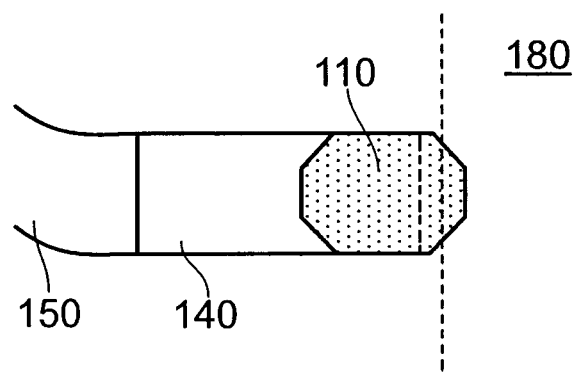
FIG. 10 shows a radiating blade structure that is another embodiment of the invention.

FIG. 10 shows an embodiment where a ceramic material 110 performs the function of impedance matching between an unloaded waveguide section 140 and the biological tissue 180. The ceramic material 110 is cut or ground to form a sharp cutting blade edge to cut through the biological tissue structure 180. In FIG. 10, the ceramic material has a relative permittivity of 6.32 at the frequency of interest to enable an effective impedance match between the unloaded waveguide cavity full of air with a relative permittivity of unity and a block of tissue 180 with a relative permittivity of 40. The proximal end of the ceramic material 110, where the energy is coupled from the waveguide cavity into the ceramic material 110 is shaped to enable maximum field coupling into the ceramic material 110.

Figure 11:
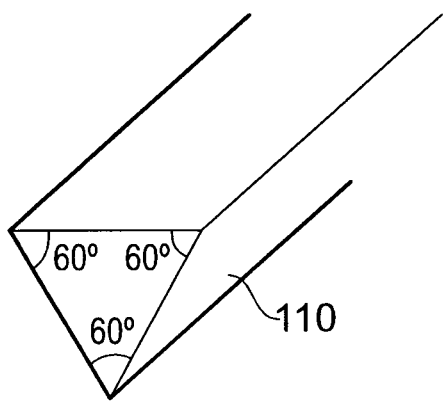
FIG. 11 shows an example of a cutting blade structure.

FIG. 11 shows a 'tooth' shape radiating blade, which takes the form of an equilateral triangle that has three equal sides and three equal angles of 60°. One of the flats is extended to enable the ceramic to be held inside the waveguide and for the microwave energy to be coupled into said ceramic. Other blade shapes can be used. For example, the rhombus, the kite, the obtuse angled triangle, the scalene triangle or the isosceles triangle.

Figure 12:
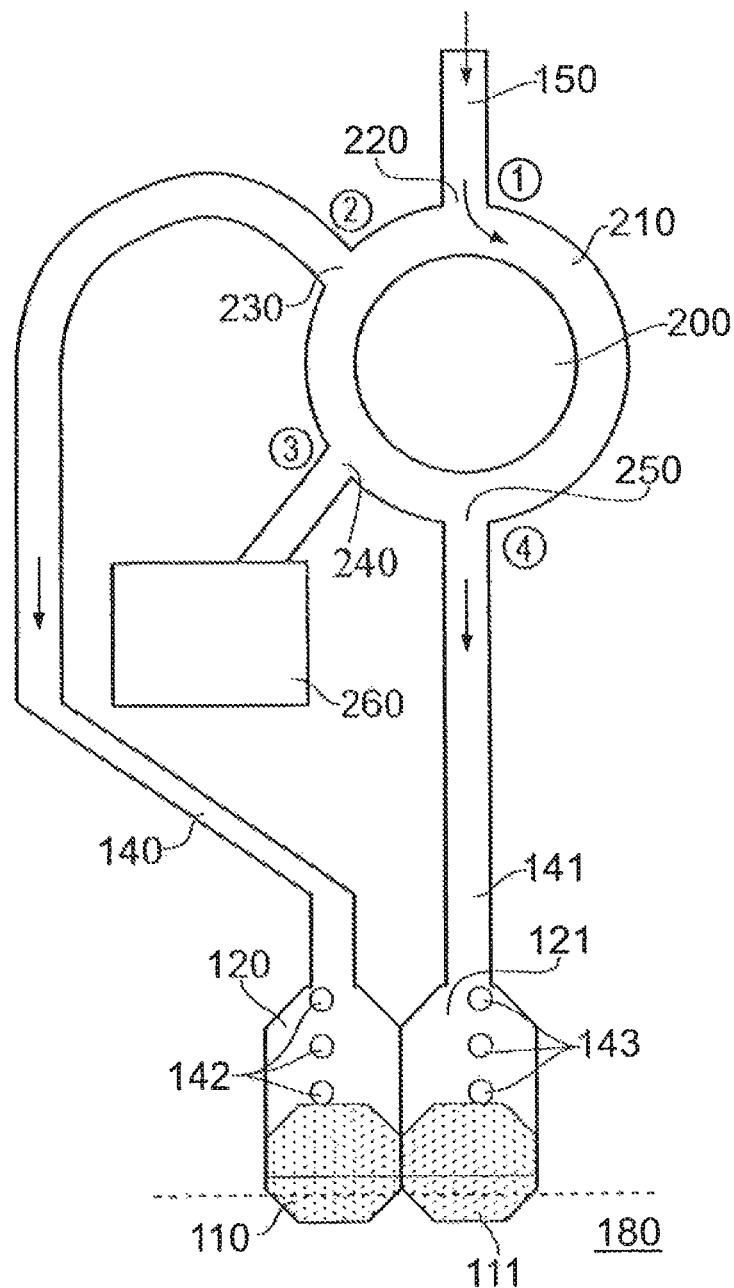
FIG. 12 shows a surgical antenna with cutting blade which is another embodiment of the invention.

FIG. 12 shows an embodiment where the surgical antenna has a blade length of around 26 mm. The device uses two 13 mm sapphire blades 110, 111 placed inside individual waveguide cavities 120, 121, with the common wall between the two pieces of sapphire made as thin as possible to ensure that the tissue effect remains uniform over the entire length of the blade. The required thickness of the wall is limited by physical constraints and the required skin depth for the microwave signal to propagate. Given that the skin depth at the frequency of interest is in the region of a few micro-meters (μm), the thickness of the wall between the two sapphire blades can be made small enough so as not to affect the uniformity of the tissue effect. The two waveguide cavities 120, 121 are independently fed using flexible or flexible-twistable waveguide assemblies 140, 141 respectively. In FIG. 12, the source power from the generator is split into two equal parts that are used to feed the proximal end of said waveguide cable assemblies 140, 141 using a Hybrid ring power splitter 200. The input power from the generator enters the Hybrid ring at port one 220. Half the output power comes out of port two 230 and the other half of the output power comes out of port four 250.

In the arrangement shown for the Hybrid ring power splitter 200, power input to port one 220 is split equally between ports two 230 and four 250, with port three 240 acting as an isolated port. The isolated port 240 is connected to a well matched power load, shown here as a waveguide load 260. In this arrangement, the phase shift between the two output ports 230, 250 is 180°. It can be said that the power splits equally around the ring 200 if all four ports 220, 230, 240, 250 have well matched loads connected to them, i.e. reflections at the ports are minimised, or the input impedance of the components connected to the four ports of the Hybrid ring (i.e. the two radiating sapphire blade antennas, the waveguide load and the input feed cable) is the same as the impedance of the input and output ports of the Hybrid ring. If said port impedance is $Z_o$ then the impedance of the ring should be equal to: $\sqrt{2} \times Z_o$, for the required conditions for an impedance matched system to be satisfied. More formally, the operation of the power splitter may be described as follows: waves at port four 250 will travel $3\lambda/4$, and so they are in phase and will add together. Waves at port two 230 will travel $\lambda/4$ and $5\lambda/4$, so they are also in phase and will add together. However, waves at port three 240 will travel $2\lambda/4$ and $\lambda$, thus these are 180° out of phase and so will cancel out. It can also be seen that the electrical length between the two output ports 230, 250 is $\lambda/2$ and so there will be a phase shift of 180° between the two output signals. This will not affect the operation of the two radiating blades 110, 111 as the two radiating antennas are working independently with the energy directed into the biological tissue and so there should be minimal interaction or coupling between the field patterns produced by the two radiating blades 110, 111. If it is desired to bring the two signals back in phase then an additional length of waveguide section can be inserted either in the path between port two 230 of the ring and waveguide cable assembly 140 or between port four 250 of the ring and waveguide assembly 141. If the electrical path length of the additional waveguide section is 180° then the waves fed into the first and second sections of waveguide launchers 120, 121 will be back in phase. Since the additional length required to produce a phase shift of 180° is around 10 mm in air (or vacuum) at the frequency of operation for the specific embodiment given here, the additional section of waveguide will not cause a significant magnitude imbalance between the two radiating blades, hence the difference in energy produced by the two blades can be ignored.

Other appropriate power couplers or power splitters may be used, some of which include: Branch line couplers, resonant cavity splitters, Wilkinson couplers and waveguide couplers, for example, a two hole coupler.

Resonant cavity splitters may be of particular interest at high microwave frequencies since these arrangements have proven to be useful in narrow band applications up to 220 GHz. In these devices, cylindrical or rectangular cavities are used to enable power losses as low as 0.2 dB and splitting efficiencies of between 85% and 90% to be achieved (ref. Kai Chang, 'Handbook of RF/Microwave Components and Engineering', Wiley-Interscience, ISBN: 0-471-39056-9, page 187).

In FIG. 12, each of the two waveguide cavities 120, 121 also contain three tuning screws 142 and 143, respectively. These tuning screws are used to enable the sapphire blades 110, 111 to be statically impedance matched with the impedance of biological tissue 180. It is desirable for the device to be impedance matched with representative biological tissue 180 that may be used in the final application, but if the device is used with the dynamic tuning system described in WO2004/047659 and shown in FIG. 2 then the impedance matching will be performed automatically. Even in this instance, it is desirable to ensure a good initial impedance match exists between the radiating sapphire blades 110, 111 and the treatment tissue 180 in order to limit standing waves, which may lead to high currents or voltages (fields) set up in the resonant cavity between the tuning network and the sapphire radiating antenna blades 110, 111, where the tuner creates the conjugate of the impedance of the tissue load to enable the matched condition to be achieved.

Microstrip (also known as strip-line) structures can also be used to feed the radiating antennas, or to act as a means of splitting the single input from the microwave power source to essentially provide a plurality of lower power sources that can be used to excite a plurality of radiating antenna structures that can be used to coagulate or ablate biological tissue.

Figure 13:
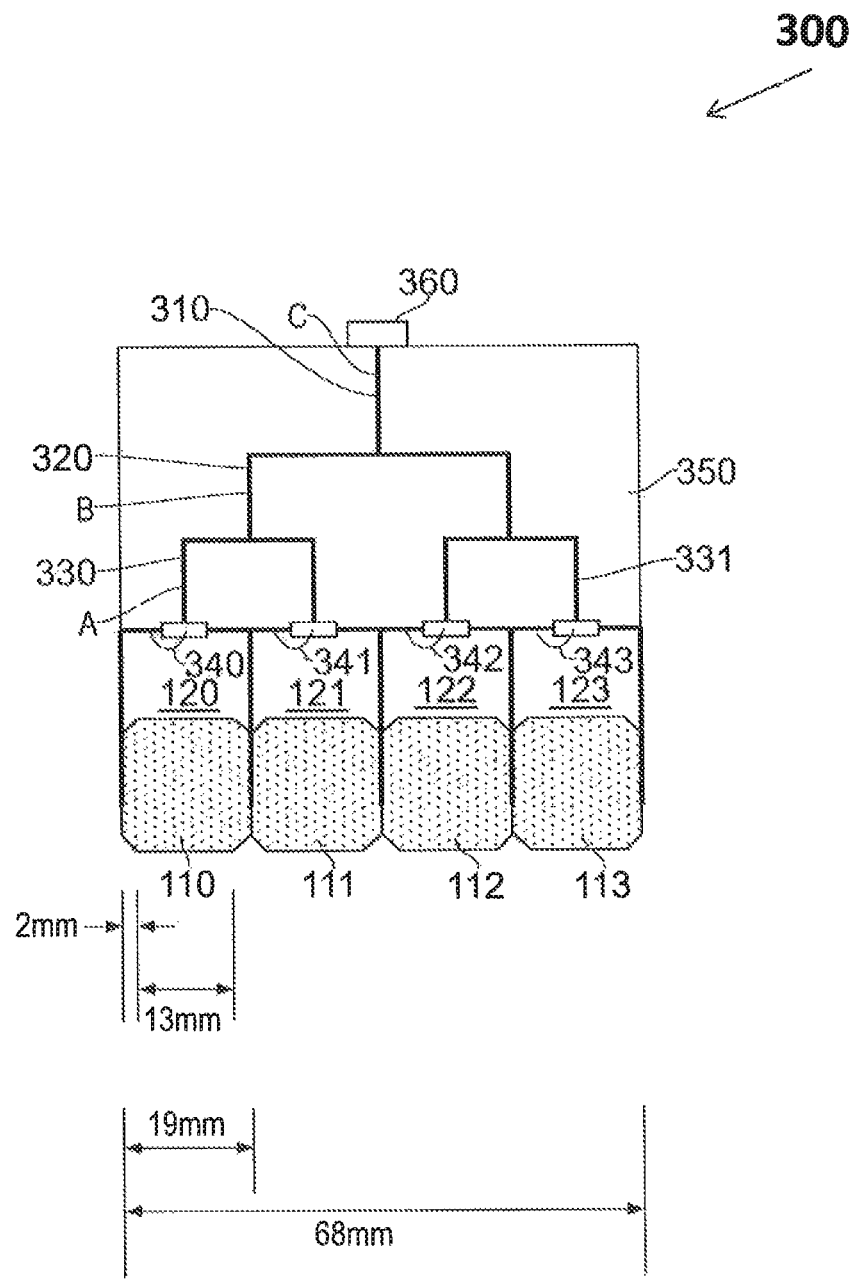
FIG. 13 shows a cutting blade comprising four antennas according to another embodiment of the invention.

FIG. 13 shows an embodiment where the cutting/radiating antenna structure has a blade length of approximately 68 mm. The design uses a microstrip feed line structure fabricated onto a dielectric material 350 that exhibits a low insertion loss at the frequency of interest and thick enough to enable power levels up to and in excess of 100 W continuous wave to flow; a suitable candidate is RT/Duriod® 5880 from Rogers Corporation, which is a PFTE glass fibre composition with a relative permittivity of 2.33 and a dissipation factor of 0.0009 at 10 GHz. A suitable thickness for this material to be capable of handling the power generated by the system is between 2.5 mm and 3.5 mm. The width and thickness of feed lines 310, 320, 330 and 331 also determines the power level that the feed line structure can handle, and since the width of the feed lines 310, 320, 330 and 331 increases with the thickness of dielectric material 350, it is desirable to make the thickness of the dielectric as large as is physically possible in order to keep the width of the track as wide as possible. The impedance for all the microstrip lines used for the feed structure shown in this embodiment is 50Ω. The surgical antenna shown in FIG. 13 uses four waveguide sections 120, 121, 122, 123 loaded with pieces of dielectric material 110, 111, 112, 113. The pieces of dielectric material are in the form of sharp blades that can be used to radiate microwave energy into biological tissue 180 and also cut through said biological tissue 180. The thickness of the inner waveguide walls between the dielectric materials is small enough to prevent discontinuity of the fields produced by adjacent dielectric material sections from causing non-uniform tissue effects, i.e. the wall between 110 and 111, the wall between 111 and 112, and the wall between 112 and 113. The microstrip feed structure consists of four 50Ω microstrip lines C310, B320, A330, A331. The input feed line C310 consists of a line that may be of any length with a microwave connector 360 connected to the input. Said connector 360 may be an N-type connector or an SMA type connector. A second microstrip line B320 connected to the distal end of feed line C310 forms two quarter wave transformers, i.e. the length of line from the distal end of feed line C310 is $(2n-1)\lambda/4$. It is assumed that the impedance connected to the distal ends of lines A330 and A331 have an impedance of 50Ω, hence the impedance seen at the distal end of the two impedance transformers produced by line B320 will be equal to two 50Ω impedances connected in parallel, i.e. 25Ω. The 50Ω quarter wave transformers B320 then transforms the 25Ω impedance to 100Ω, i.e. $50^2/25=100\Omega$, and since the proximal end of the two impedance transformers formed by line B320 is connected to the distal end of feed line C 310, the impedance seen at the distal end of feed line C 310 is equal to two 100Ω impedances connected in parallel to give 50Ω, hence the feed network is impedance matched to the 50Ω system. Microstrip lines A330, A331 can be of any practical length, but the lengths from the centre point where they are connected to transformer B320 should be the same, i.e. the phases and magnitudes of the energy at the two ends of lines A 330 and A 331 are also the same. The energy from the four ends of microstrip lines A330 and A331 is coupled into waveguide cavities 120, 121, 122, 123 using 'H'-field loops 340, 341, 342, 343. The loops have a length equal to a half of the wavelength (or an odd multiple thereof) at the frequency of interest. One end of the loop is connected to one of the four outputs of the microstrip power splitter and the other end is connected to the wall of the respective waveguide cavity. The 'H' field loops enable transverse magnetic (TM) or transverse electric (TE) fields to be set-up inside the waveguide, hence the transverse electromagnetic (TEM) wave set-up along the microstrip line structure is converted into a transverse magnetic (TM) wave or a transverse electric (TE) wave set-up inside the four waveguide cavities 120, 121, 122, 123. Whether the wave set-up is a TM or a TE wave is dependent upon the orientation of the loop; the orientation shown in FIG. 13 will set-up a TM wave, whereas if the loops were to be turned through 90° then a TE wave will be set-up. An alternative to using loop coupling is to use probe coupling, where a probe that normally has a length equal to a quarter of the wavelength at the frequency of interest is inserted through the wall of the waveguide. When 'H'-field loops are used, the magnetic field is generally predominant, and so the waveguide is termed transverse magnetic, where magnetic lines go through the centre of the loop. It can be seen from FIG. 13 that there is a gap between the microstrip lines and the waveguide cavities; this gap ensures that the signal line (or power feed) does not short circuit to the wall of the waveguide cavities. The bottom side (second side) of dielectric substrate material 350 is metallised over its whole surface to form a ground plane and this metallised surface is electrically (and physically) connected to the outer walls of waveguide cavities 120, 121, 122, 123.

A second dielectric material can be sandwiched onto the top of microstrip feed line structure C310, B320, A330, A331 to prevent the feed line structure from radiating into free space. In this instance, the second side of second dielectric material is metallised over its whole surface to form a ground plane and this metallised surface is electrically (and physically) connected to the outer walls of waveguide cavities 120, 121, 122, 123. In this instance the width of the microstrip lines is modified to take into account the second dielectric material. If the thickness of the second dielectric material is the same as that of first dielectric material, i.e. 350, then the line width is approximately halved.

In order for the microstrip feed structure to be capable of handling continuous wave power levels up to and in excess of 100 W, it is preferable for the thickness of the microstrip lines to be around 2 oz (70 μm) and for the line material to have a high conductivity, for example, copper, brass, gold or silver may be used.

Figure 14:
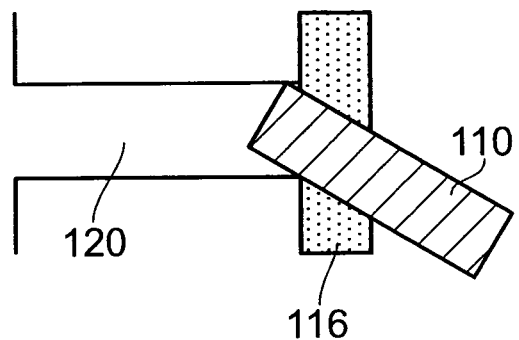
FIG. 14 shows a surgical antenna with cutting blade held in position using foam in another embodiment of the invention.

FIG. 14 shows an arrangement for a surgical antenna using a sapphire blade 110 inserted into a waveguide cavity 120 and held in position using a piece of Styrofoam 116. The sapphire blade 110 is positioned inside waveguide cavity 120 in such a manner that the maximum field generated inside the waveguide cavity is coupled into the radiating blade 110 to enable the maximum energy to be available for treating tissue structures 180. All of the surface area of the sapphire except for the radiating blade section and the section inside waveguide cavity 120 where the microwave field is coupled into the material is metallised. The layer of metallisation prevents the surface of the material from radiating into free-space, and also helps to focus the fields into the biological tissue structures 180.

Figure 15:
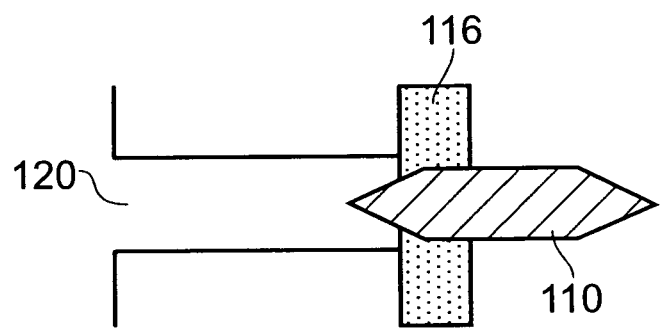
FIG. 15 shows a surgical antenna with cutting blade held in position using foam in yet another embodiment of the invention.

FIG. 15 shows a cylindrical ceramic radiating blade 110 inserted inside a waveguide cavity 120 and held in place using a piece of Styrofoam 116. In this arrangement, the radiating section is a cone that is metallised up to the radiating tip. The ceramic section inside waveguide cavity 120 is a pointed section to enable maximum field coupling from the waveguide cavity into the ceramic rod. The ceramic section inside the waveguide is not metallised. The external point is sharp to enable the structure to puncture through the skin or to be pushed through biological tissue structures comprising of a plurality of anatomical planes unaided. A blade (e.g. a scalpel blade) can be fixed to the end tip of the cone to enable and/or assist with tissue cutting or to make the initial incision (this is not shown in FIG. 15).

FIGS. 16 to 19 provide details of possible devices that may use microstrip antenna structures and feed lines to provide the required cutting and sealing features of the invention.

The structures given in FIGS. 16 to 19 can be implemented using strip-line or triplate microstrip structures in order to shield the feed structures associated with the designs to prevent radiation coming off of the feed structures and also to minimise discontinuities.

Figure 16:
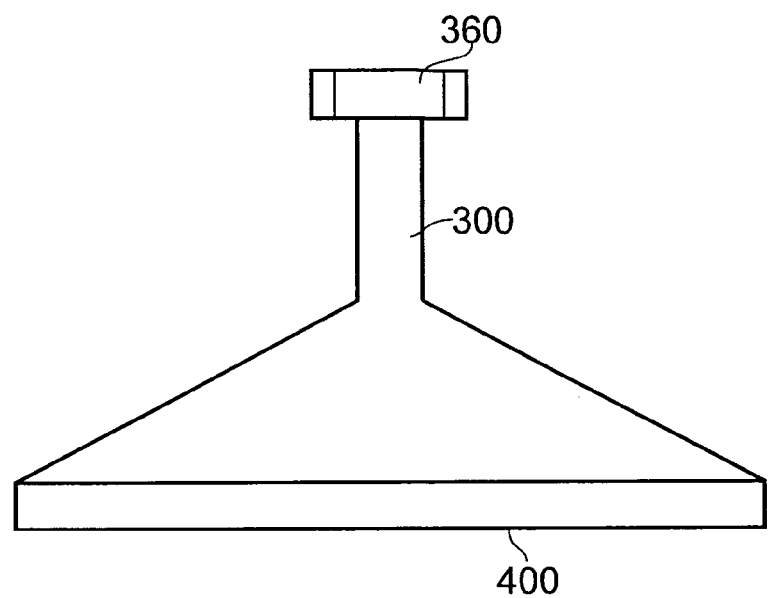
FIG. 16 shows a surgical antenna with a 'paint stripper' structure that is another embodiment of the invention.

FIG. 16 shows an embodiment of a liver resection antenna that uses a 'paint stripper' structure with an array of radiating patch antennas 400 deposited onto a blade to form a radiating section that can produce a uniform radiation pattern along the length of the blade to produce uniform tissue ablation as the structure is pushed into biological tissue. The radiating elements can assist with the tissue cutting process. The impedance of the radiating elements is matched to the impedance of the biological tissue to enable the blade to efficiently deliver energy into the tissue to, for example, coagulate blood to stop bleeding when treating highly perfused organs within the human body. A microwave connector 360 is used to launch the microwave energy into the radiating structure and a feed line structure 300 is used to feed each of the radiating patch antennas preferably with the same level of power. The feed lines enter the patch antennas in such a manner that the phase of the signals are the same, and adjacent patches are in close proximity to provide a uniform tissue effect along the length of the radiating blade.

Figure 17:
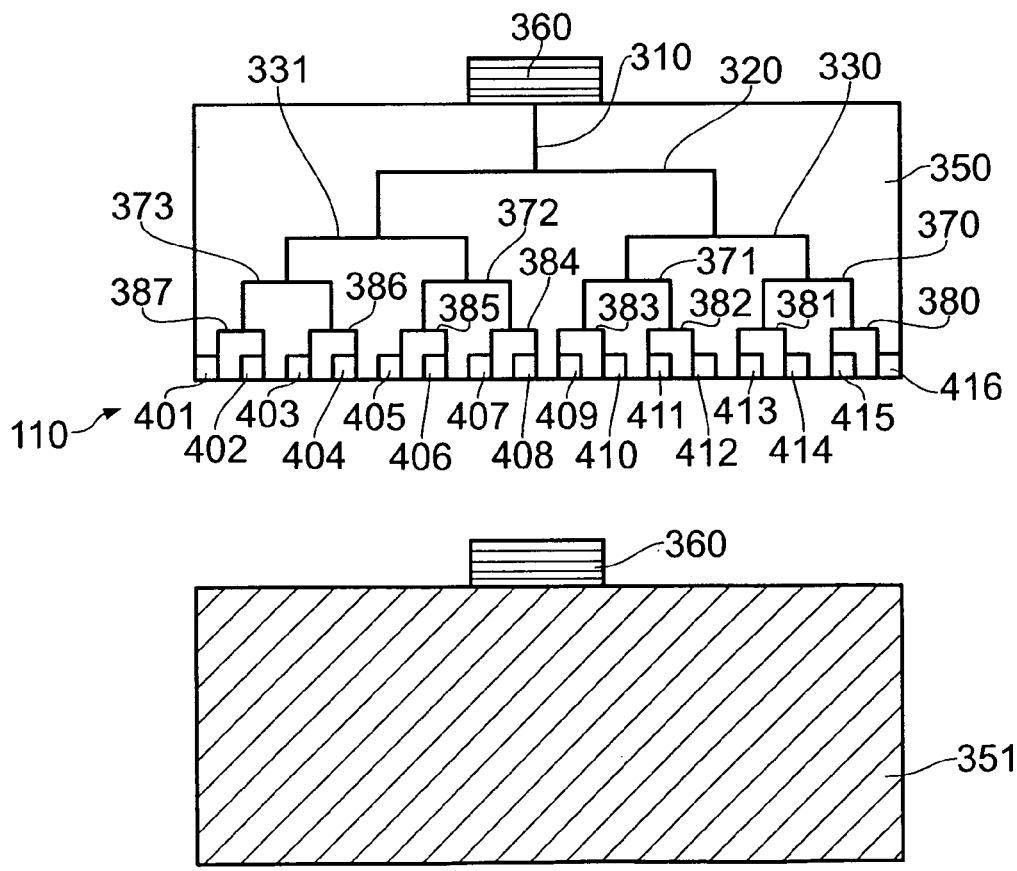
FIG. 17 shows a radiating blade antenna with a plurality of patch antennas fabricated thereon, which is another embodiment of the invention.

FIG. 17 shows a detailed embodiment of a radiating blade antenna having a plurality of radiating patch antennas. The antennas and a feed line structure are deposited onto one side of a ceramic substrate material (blade) 350 with the second side of said substrate material 350 fully metallised to form a ground plane or return path 351. The embodiment shown in FIG. 17 uses sixteen radiating patch antennas 401-416 disposed along the edge of the ceramic blade. The feed structure uses 50Ω microstrip lines and alternate quarter wave transformers. An N-type microwave connector 360 is connected to the input of the feed line structure and enables a cable assembly to be connected between the microwave power generator and the surgical antenna. First microstrip line 310 is connected to the microstrip launch pin of microwave connector 360. The length of said microstrip line 310 is not critical, but is governed by the tolerable insertion loss and physical constraints relating to the end use and general aesthetics of the instrument that apply. The distal end of microstrip line 310 is connected to second microstrip line 320, which forms two quarter wave transformers. The centre point of second microstrip line 320 connects to the distal end of first microstrip line 310. The two distal ends of second microstrip line 320 are connected to the centre point of third and fourth microstrip lines 331, 330 respectively. The length of third and fourth microstrip lines 331, 330 is not critical, but it is preferable that the two line lengths are the same to enable the signals at the four distal ends to be the same in terms of magnitude and phase. The distal ends of third and fourth microstrip lines 331, 330 are connected to the centre point of fifth, sixth, seventh and eighth microstrip lines, which form a further four half wavelength microstrip lines 373, 372, 371, 370 respectively. These microstrip lines form a further eight quarter wavelength transformers. The distal ends of the four half wavelength microstrip lines 373, 372, 371, 370 are connected to a further eight microstrip lines 380, 381, 382, 383, 384, 385, 386, 387, whose length are not critical, but should preferably all be of the same length in order to ensure that the phase and magnitude of all of the signals produced at the distal end of said microstrip lines are the same. The distal ends of microstrip lines 370-373 should be connected to centre point of microstrip lines 380-387 to enable the necessary impedance transformations to be performed. The distal ends of microstrip lines 380-387 form the feed lines to radiating patch antennas 401-416 respectively.

The distance between adjacent radiating patches is such that a uniform electromagnetic field is generated along the length of the blade. The distance between adjacent patches is around 1 mm at the frequency of interest in order to ensure that the tissue effect (coagulation/ablation) is uniform along the length of the radiating blade.

An example of the operation of the 50Ω microstrip feed line structure given in FIG. 17 is as follows:

1. Starting at the feed to the sixteen radiating antennas, assume that antenna feed points 401-416 'see' a load of impedance of 50Ω,
2. This implies that the centre point of microstrip lines 380-387 each 'see' an impedance of 25Ω, i.e. two 50Ω loads in parallel (50/2=25Ω),
3. As microstrip lines 370-373 are each an electrical length equal of a half of the wavelength at the frequency of interest and the centre of the lines are connected to the distal end of the microstrip lines that feed these lines, each of the 25Ω load impedances are transformed to 100Ω by each of the quarter wavelength transformers, i.e.

$$Z_0=\sqrt{(Z_1 \times Z_s)} => Z_1 = Z_0^2/Z_s = 50^2/25 = 100\Omega$$

(in this analysis $Z_o$ is the characteristic impedance of the microstrip line (in ohms), $Z_1$ is the load impedance (in ohms) and $Z_s$ is the source impedance (in ohms)), 4. This implies that the impedance 'seen' at the centre point of each of the microstrip lines 370-373 is 50Ω, i.e. the parallel sum of the two 100Ω impedances (100/2=50Ω),
5. Therefore, the impedance 'seen' at the four distal ends of microstrip lines 331 and 330 is 50Ω,
6. This implies that the centre point of microstrip lines 331 and 330 'see' an impedance of 25Ω, i.e. two 50Ω loads in parallel (50/2=25Ω),
7. Microstrip line 320 has an electrical length equal to a half of the wavelength at the frequency of interest, and the centre of line 320 is connected to the distal end of first microstrip feed line 310 that connects to input connector 360; therefore, the 25Ω load impedance is transformed to 100Ω by the quarter wavelength transformer, i.e.

$$Z_1 = Z_o^2/Z_s = 50^2/25 = 100\Omega$$

8. This implies that the impedance 'seen' at the centre point of the microstrip line 320 is 50Ω, i.e. the parallel sum of the two 100Ω impedances (100/2=50Ω)
9. Given that first microstrip line 310 is a 50Ω microstrip transmission line and the cable assembly connected to input connector 360 has a characteristic impedance of 50Ω, the 50 Ω impedance 'seen' at the centre point of microstrip line 320 provides the conditions for a well matched network or system Radiating patch antennas 401-416 are configured such that the radiating edges are impedance matched to the impedance of the biological tissue 180 that is in contact with said radiating edges.

Figure 18:
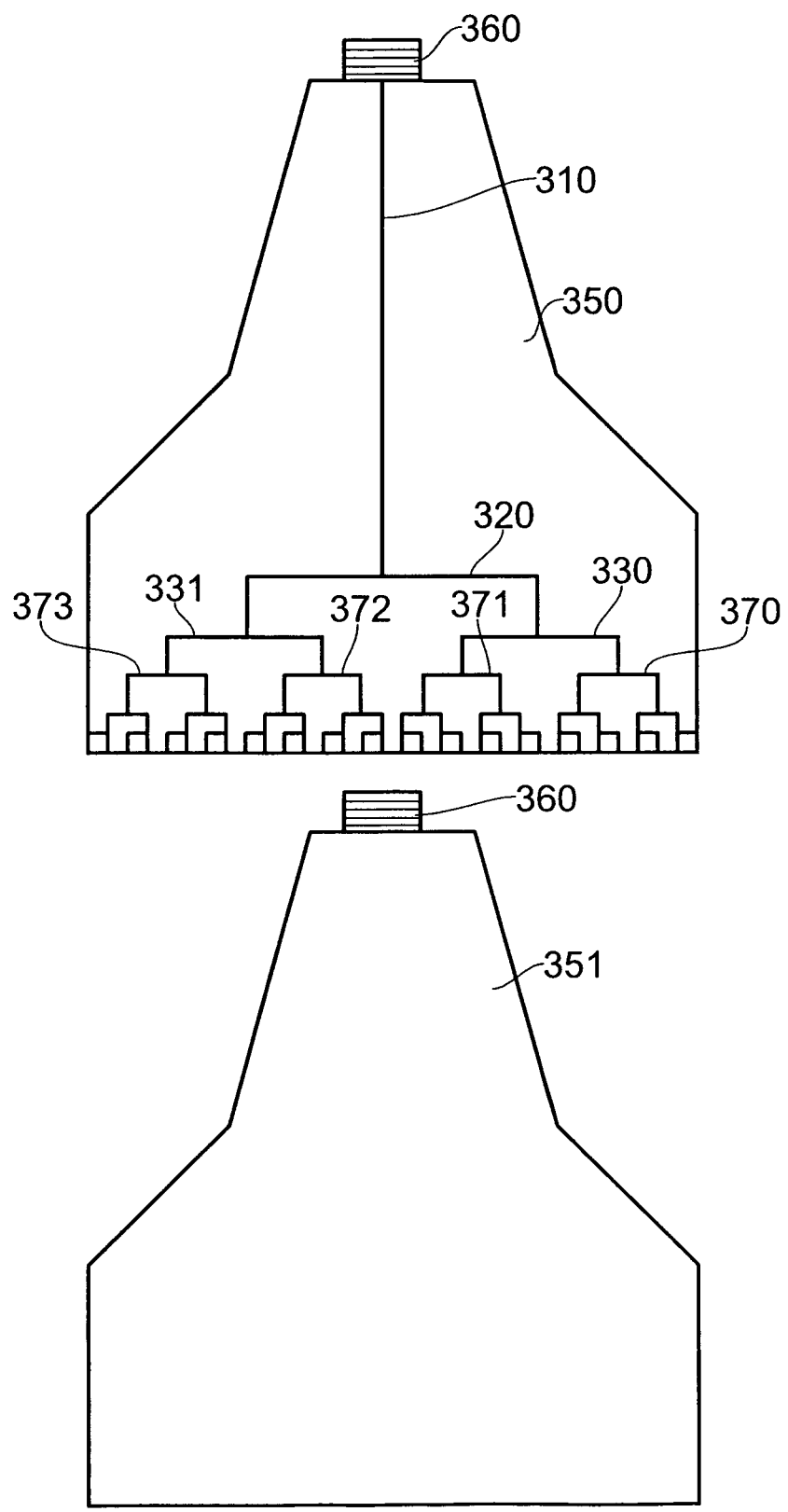
FIG. 18 shows a radiating blade antenna with a plurality of patch antennas fabricated thereon that is yet another embodiment of the invention.

FIG. 18 shows an alternative arrangement for a surgical resection antenna that uses a microstrip feed line structure and a plurality of radiating patch antennas fabricated onto the first side of a hybrid substrate structure. In this arrangement the first four microstrip lines 310, 320, 331, 330 that form a part of the feed line structure is fabricated onto a microwave PCB material; in this embodiment, the microwave PCB material is a 5880 RT Duriode® from Rogers Corporation. The remaining feed lines 380-387 and the radiating antenna elements 401-416 are fabricated onto a hard ceramic material, which, in this embodiment is sapphire. The two materials may be bonded using a suitable adhesive. The second side of the structure is fully metallised and forms a ground plane or return signal 351 for the microwave feed and the radiating antenna structure. The metallisation layer is a good conductor, for example, copper, silver or brass. An interface layer is provided between the metallisation and the substrate material in order to bond the two layers together. The interface material exhibits a low loss at the frequency of operation in order to prevent a portion of the microwave energy being absorbed by the material and causing the undesirable effects of structural heating and loss of energy available at the radiating antennas.

The feed lines can be covered with a metallic enclosure (not shown) to prevent emissions of radiation from the microstrip feed line structure propagating into free-space.

Figure 19:
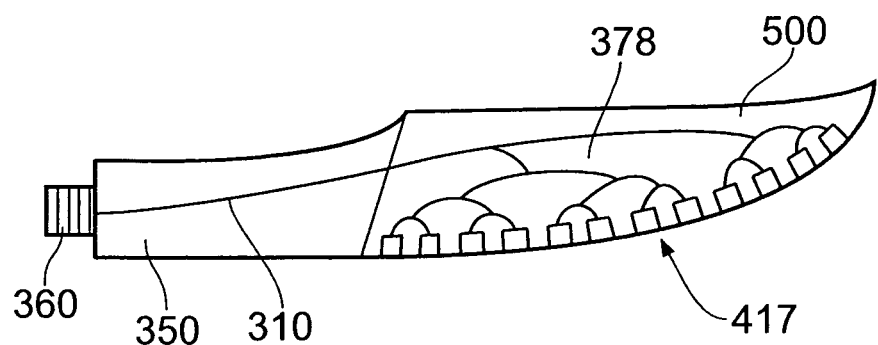
FIG. 19 shows a scalpel having a plurality of patch antennas fabricated at the blade edge.

FIG. 19 shows an embodiment of the radiating patch antenna structure with a feed structure 378 and radiating patches 417 fabricated onto a scalpel blade 500. One side of the scalpel blade is used as the ground plane and a layer of dielectric substrate material 350 is attached to the second side of the scalpel blade, whereby the microstrip feed line structure and the radiating patches are attached to said substrate layer to form a microstrip line structure. A spray on dielectric material can be used to coat the second side of scalpel blade 500 before attaching a layer of metallisation for the microstrip feed lines and the radiating patches.

The geometry of the radiating patch antennas shown in FIGS. 17 to 19 is determined by the operating frequency, the properties of the substrate material, and the tissue load. In normal operation the radiating edge of a patch antenna is a half the wavelength at the operating frequency. Typically, the fields along the edges perpendicular to the feed line are zero.

Figure 20A:
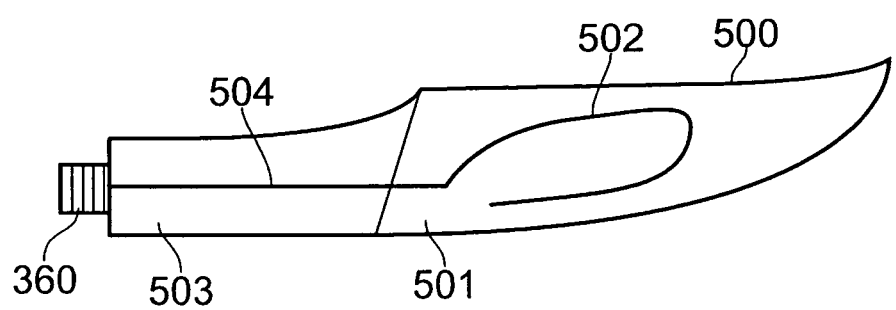
FIG. 20(a) shows a scalpel having an H-field loop antenna attached thereto.
Figure 20B:
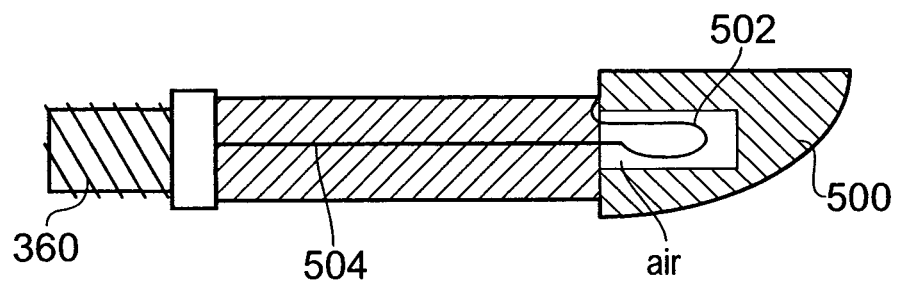
FIG. 20(b) shows a scalpel having an H-field loop antenna attached thereto with the centre of the blade removed to enable the electromagnetic energy to propagate around the blade.
Figure 20C:
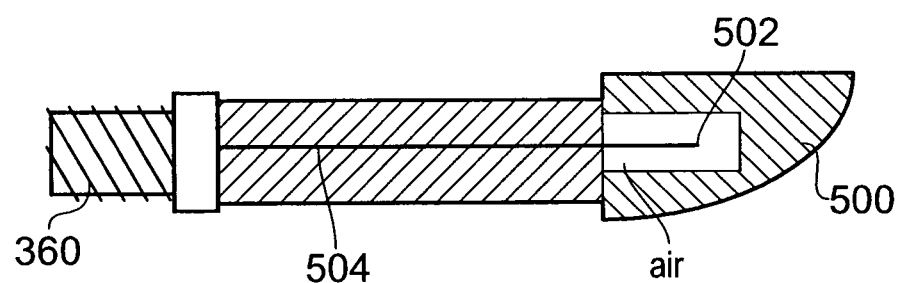
FIG. 20(c) shows a scalpel having an E-field probe antenna attached thereto with the centre of the blade removed to enable the electromagnetic energy to propagate around the blade.

FIG. 20(a) shows a further embodiment for a radiating blade antenna. In this arrangement a scalpel blade 500 is attached to the distal end of a co-axial cable assembly 503, 504 and a radiating 'H'-field loop antenna 502 is attached to the distal end of said co-axial assembly to form a radiating field element. The centre conductor 504 is connected to the proximal end of 'H'-field loop 502 and the distal end is attached to the outer conductor 503 of the co-axial feed structure. An insulation material 501 is used to prevent the 'H'-field loop from shorting to cutting blade 500. The embodiment shown here uses Kapton tape as the insulation material due to its high voltage breakdown capacity, but other insulators can be used. In operation, the sharp edge of the blade cuts through tissue and the loop antenna radiates microwave energy to instantly ablate or coagulate tissue 180 in the vicinity of the cutting edge. The physical length of the 'H'-field loop is a half the wavelength at the preferred frequency of operation (or an odd multiple thereof). The diameter of the loop of wire is capable of handling power levels of up to 100 W continuous wave. As an alternative to the 'H'-field loop, an 'E' field probe antenna may be used to produce the microwave radiation. For example, monopole, dipole, turnstile or spiral antenna structures may be attached to the blade structure. The radiating structure can be partially screened to limit electromagnetic field emissions into free space or to limit the risk of radiation to the user or to the patient in regions of the anatomy other than the desired treatment zone. The arrangement shown in FIG. 20(a) may be modified by removing a section around the centre of cutting blade 500 where 'H'-field antenna 502 is located. Said 'H'-field antenna 502 may then reside inside the centre section of said cutting blade 500 to enable a radiating electromagnetic field to be produced around the cutting edge of cutting blade 500 that can be used to seal off blood flow in the vicinity of the cutting edge. This arrangement is shown in FIG. 20(b), where it can be seen that insulation material 501 has been removed and the radiating loop is located inside cut-out section of blade 500. Said blade 500 may be made from a hard ceramic material or a metal. FIGS. 20(b) and 20(c) show embodiments of scalpel blade antennas with an 'H'-field loop antenna and an 'E'-field probe or monopole antenna respectively. Each of these embodiments have a section of the blade removed to enable the microwave radiation to propagate around the cutting edge of the blade.

FIG. 21 provides embodiments of loaded waveguide antenna arrangements with static tuning elements to enable the antenna structures to be impedance matched with the impedance of the biological tissue loads. The antenna structures shown here are for use in treatment applications and, more specifically, for use in treating large solid tumours, for example, liver tumours, lung tumours or adrenal tumours. FIG. 21(a) shows a loaded waveguide antenna structure where a portion of a radiating dielectric rod 601 is inserted into biological tissue 180 to cause tissue ablation. In this arrangement the dielectric rod 601 acts as an impedance transformer to enable the impedance of waveguide cavity 602 to be impedance matched to the impedance of biological tissue 180. Dielectric rod 601 fits inside cylindrical waveguide section 600 and said cylindrical waveguide section 600 is connected to rectangular waveguide section 602. The rectangular section 602 contains three tuning stubs 141, 142, 143, which are used to match waveguide cavity 602 to the impedance 'seen' at the distal end of dielectric material 601 to enable maximum power transfer between the energy source and the biological tissue load 180. The input microwave power is coupled into the antenna using a microwave connector, which has one end of an 'H'-field loop 603 connected to its centre conductor (pin). The other end of the loop is connected to the wall of waveguide 602. The length of said loop 603 is equal to a half of the wavelength at the preferred frequency of operation (or an odd multiple thereof). This 'H'-field loop coupling arrangement enables the cable assembly used to provide the microwave power to the antenna to be connected to the assembly in the same plane as the antenna, i.e. the antenna structure is 'end fed'. The spacing between adjacent tuning stubs 141, 142 or 142, 143 is a quarter of the guide wavelength determined by the cut-off frequency of the rectangular waveguide section 602 and the frequency of operation.

Figure 21A:
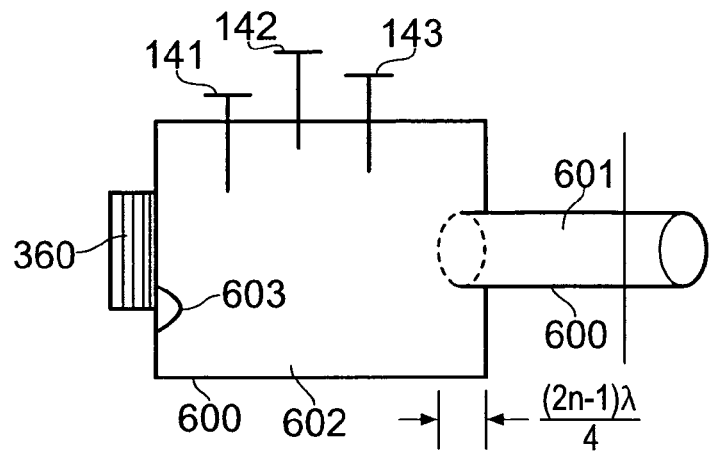
FIGS. 21(a)-(d) show tunable loaded waveguide antennas for treating tumours, which are further embodiments of the invention.
Figure 21B:
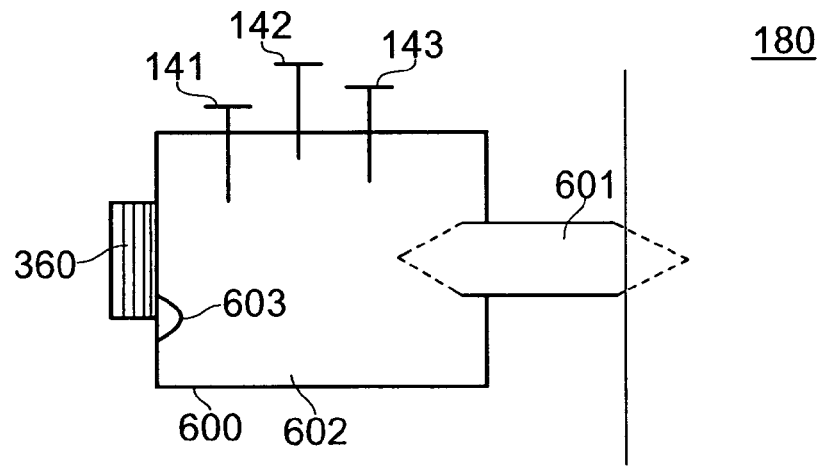

FIG. 21(b) shows a similar arrangement to that shown in FIG. 21(a) except that in the arrangement shown in FIG. 21(b), dielectric rod 601 is tapered along its length from the distal end of cylindrical waveguide section 600. The proximal end of dielectric rod 601 is also shown with a taper to produce a tapered launch from waveguide cavity 602 into the dielectric rod. It is preferable for dielectric rod 601 to be a low loss material, i.e. the dissipation factor at the frequency of interest should be less than 0.001 for example.

Figure 21C:
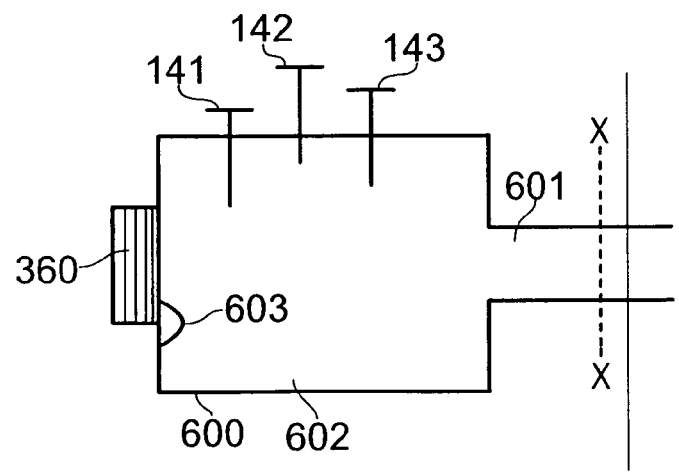
Figure 21D:
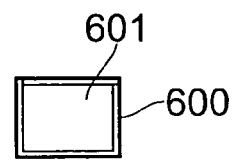

FIG. 21(c) shows a loaded rectangular antenna arrangement, where the shape of radiating dielectric material 601 is rectangular. All the features of the antenna structure shown in FIG. 21(c) are identical to the antenna structures shown in FIGS. 21(a)&(b) described above. FIG. 21(d) shows a cross-section of the radiating face of the antenna structure. It can be seen that the radiating face sits on the surface of the tissue structure 180 to be treated. This invention is not limited to using rectangular shaped rods; square shaped rods or even triangular shaped rods can be used. The structures shown in FIGS. 21(*a*) and (*c*) may be used to launch energy into tissue structures that are located underneath the surface of the tissue that the antenna is in physical contact with. For example, the radiating section of the antenna (cylindrical or rectangular) may sit on the surface of the skin and the microwave energy may be used to change the state of fatty tissue located underneath the surface of the skin while leaving the upper surface of the skin (the epidermis) unadulterated. The surface of the skin (or other tissue structure) can be cooled whilst applying the microwave energy in order to ensure that the tissue structure at and/or close to the surface is preserved.

Figure 22:
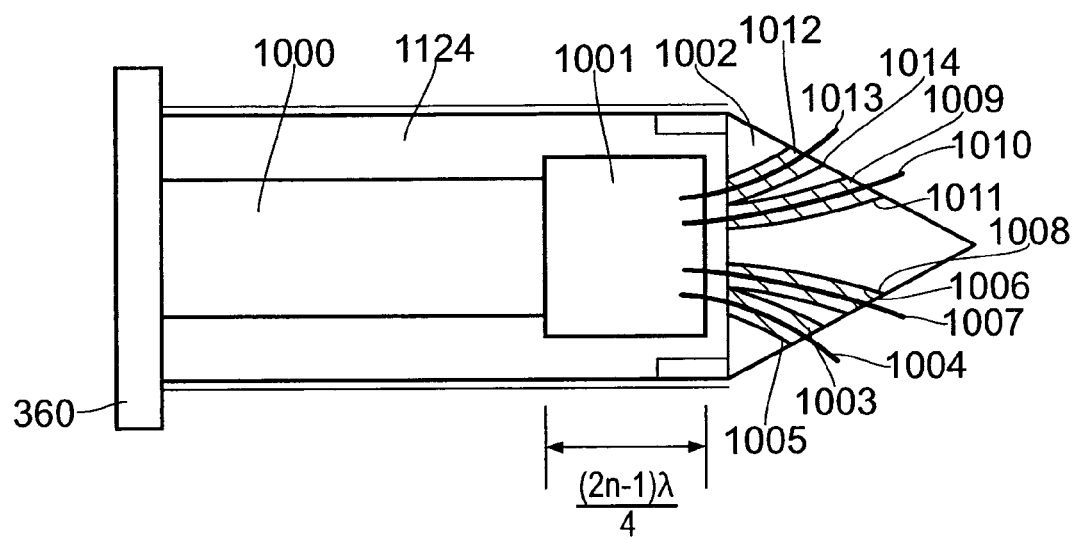
FIG. 22 is an ablation antenna structure for treating large tumours that is another embodiment of the invention.
Figure 23:
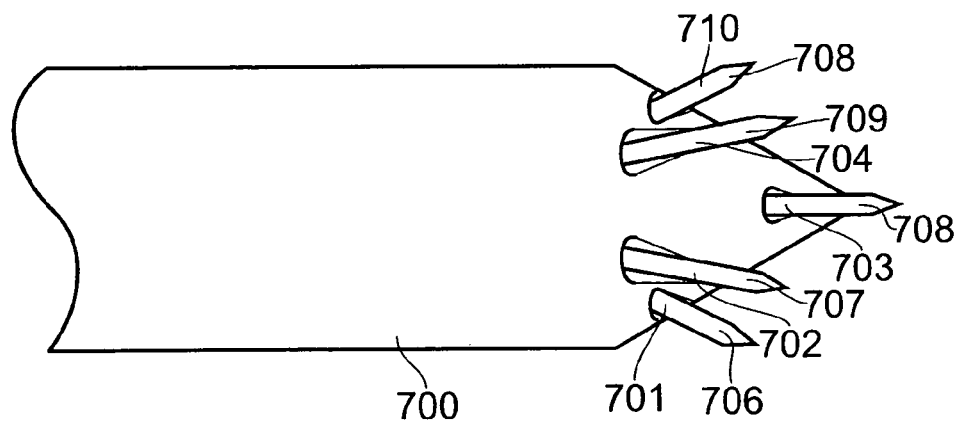
FIG. 23 shows a concept drawing for an antenna structure suitable for treating large volume solid tumours.
Figure 24A:
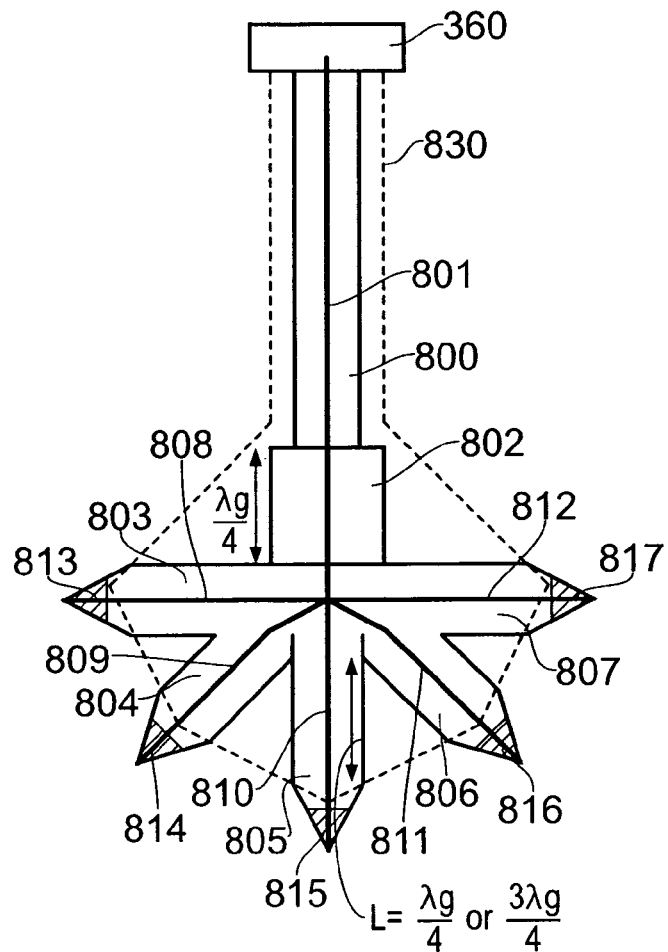
FIGS. 24(a)-(b) show a coaxial antenna structure that may be used for the ablation of liver tumours.
Figure 24B:
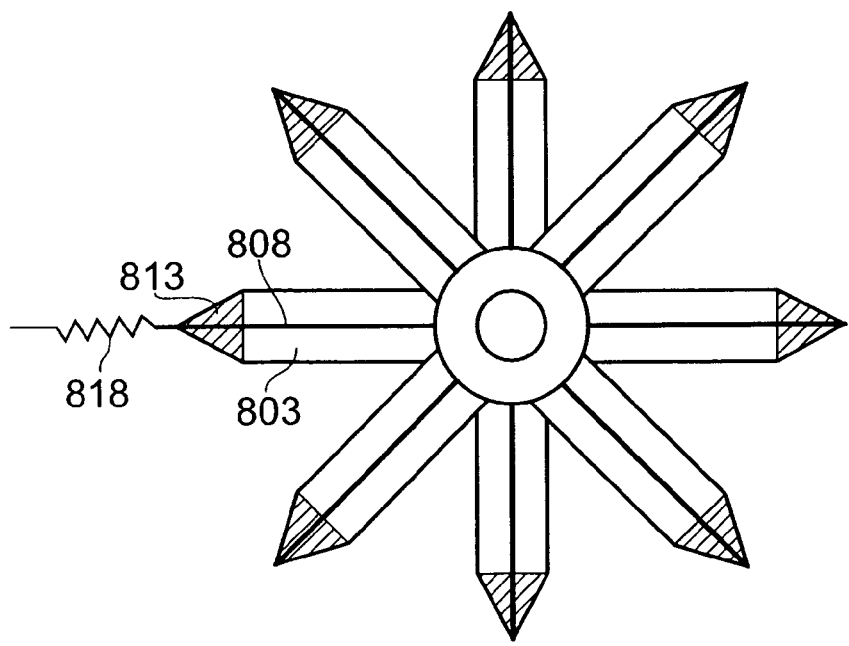

FIGS. 22 to 24 show antenna structures that may be used to treat large volume solid tumours located within the human and animal body. The structures introduced here are based on co-axial and microstrip transmission line systems with quarter wave impedance matching transformers. FIG. 23 shows a concept drawing of an antenna structure that comprises a plurality of co-axial radiating antenna structures 701/706, 702/707, 703/708, 704/709, 705/710 arranged to radiate from the end of a tube or trocar or catheter 700. The distal end of said tube is cone shaped and the co-axial radiators are arranged in such a manner that they produce a uniform electromagnetic field over the surface of the cone in order to produce uniform tissue effects when inserted inside biological tissue structures 180. The plurality of coaxial radiating structures are fed from a single co-axial cable that is capable of handling the total power delivered at the end of the structure without excessive insertion loss, i.e. for 100 W continuous power to be launched into the input of the antenna structure, the outside diameter of the structure is around 10 mm.

FIGS. 24(*a*)&(*b*) shows an arrangement for a co-axial treatment antenna structure that may be used for the ablation of liver tumours. The structure consists of a first co-axial feed cable 801 with a microwave connector 360 connected to the proximal end, a second co-axial cable section 802 arranged as an impedance transformer, and a further eight co-axial cable assemblies (only five of which are visible in FIG. 24(*a*)) 808-812 with radiating ends 813-817. Second co-axial cable assembly 802 has a physical length that is equal to the electrical length of a quarter of the wavelength (or an odd multiple thereof) at the frequency of operation and of an impedance that is equal to the square root of the product of the characteristic impedance of first co-axial section 801 and the parallel sum of the impedance of the eight co-axial cables with the radiating ends connected to representative tissue loads.

The characteristic impedance of second co-axial cable assembly 802 that performs the required impedance transformation can be calculated for any number of co-axial radiators using $$Z_{o2} = \sqrt{(Z_{o1} \times Z_{o3}^2 / Z_1 \times n)}$$

where $Z_{o2}$ is the characteristic impedance of co-axial transformer section 802 (Ω), $Z_{o1}$ is the characteristic impedance of co-axial feed cable 801 (Ω), $Z_{o3}$ is the characteristic impedance of 'n' co-axial cable sections connected to the distal end of 802 (Ω), $Z_1$ is the impedance of the tissue load (Ω), and 'n' is the number of radiating elements (no units).

This analysis assumes that each radiating end 'sees' the same load impedance, i.e. the impedance of the biological tissue is the same over the region where the radiating elements make contact, or, put another way, the load is balanced.

This analysis also assumes that the characteristic impedance of each of the co-axial sections ($Z_{o3}$) is the same, and that the length of the co-axial cable sections denoted by $Z_{o3}$ is a quarter of the wavelength at the operating frequency (or an odd multiple thereof).

The arrangement shown in FIG. 24 may be inserted inside a tube and the radiating elements may be arranged inside a cone shape structure as illustrated in FIG. 23.

FIG. 22 shows a further antenna structure that may be used to ablate large volume tumours. This arrangement uses a microstrip transmission line 1000, with a microwave input connector 360 connected at the proximal end and a microstrip impedance transformer 1001 connected at the distal end. The microstrip impedance transformer 1001 is a quarter wave transformer that has a physical length equal to a quarter of the electrical wavelength (or an odd multiple thereof) at the frequency of operation where this length takes into account the relative permittivity of substrate material 1124. Said microstrip lines 1000, 1001 are fabricated onto the first side of a suitable microwave substrate material 1124. The second side of said microstrip material 1124 is metallised over the complete surface of the material and this layer of metallisation acts as a ground plane. Several co-axial cable assemblies, each comprising an outer conductor 1005, 1008, 1011, 1014, an inner conductor 1004, 1007, 1010, 1013, and dielectric material 1003, 1006, 1009, 1012, are connected to the distal end of impedance transformer 1001. The seven co-axial cable assemblies are mounted inside a ceramic cone 1002 and said ceramic cone 1002 is connected to the distal end of microstrip structure 1000, 1124, 1001. The seven co-axial cable assemblies are arranged (fitted) inside ceramic cone 1002 in a manner that enables ceramic cone 1002 to act as an antenna that produces a uniform electromagnetic field over the surface area of the cone tip. Metallic plates (not shown) can be connected to inner conductors 1003, 1007, 1010, 1013, to enhance the uniformity of the field produced by radiating cone 1002. The radiating cone may be insertable inside biological tissue 180 to ablate diseased or cancerous tissue structures.

Further embodiments of a surgical instrument according to an aspect of the invention are discussed below. In particular, the embodiments described below provide a resection tool having a shape similar to a scalpel blade. The shape is selected to provide a balance between the desire for a sharp cutting edge and a radiating structure that provides good coupling of microwave radiation into tissue. A particular advantage of the shape disclosed herein is that the radiating field distribution (and hence the power delivered into tissue) is substantially uniform along the cutting edge of the blade. Microwave simulations demonstrating this effect are described below.

In embodiments where the antenna is a loaded waveguide structure, i.e. the blade is a piece of dielectric material mounted on the end of a waveguide cavity to radiate microwave energy transported by the waveguide it is desirable for the dielectric material to act as an impedance matching transformer to match the impedance of the (unloaded) waveguide to the impedance of the biological tissue load to enable efficient energy delivery into the tissue. In an embodiment discussed above, a tuning arrangement (e.g. a tuning filter comprising a number of adjustable tuning stubs) is provided in a waveguide cavity to enable the antenna to be statically impedance matched with various tissue loads (e.g. different tissue types). In that embodiment, a three stub screw tuner is located between the waveguide cable assembly and the proximal end of a ceramic blade. In such a structure, the impedance mismatches within the cavity (e.g. caused by the inductive or capacitive reactance of the stubs) can cause high electromagnetic fields to build in the region of the tuning filter. These fields may lead to heating of the surgical instrument.

The embodiments disclosed below may also provide a transformer arrangement to match the impedance of the (unloaded) waveguide with the impedance of biological tissue. The transformer may form an integral part of the cutting blade. Using this transformer enables virtually all energy delivered along the waveguide to be transferred into the biological tissue.

Figure 25:
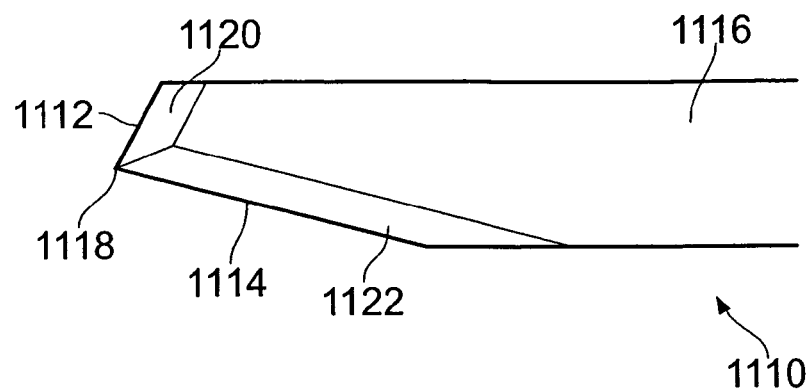
FIG. 25 is a side view of a blade structure that is another embodiment of the invention.

FIG. 25 is a side view of a radiating blade structure for a surgical antenna according to an embodiment of the invention that is particularly suitable for operation at 24 GHz. The blade structure 1110 has the basic form of a scalpel, where two sharp angled cutting edges 1112, 1114 are machined at one end of a rectangular block 1116 of material, e.g. alumina, sapphire or the like. The particular dimensions in this embodiment are suitable for alumina, but only minor alterations are needed for a similar implementation using sapphire.

Figure 26:
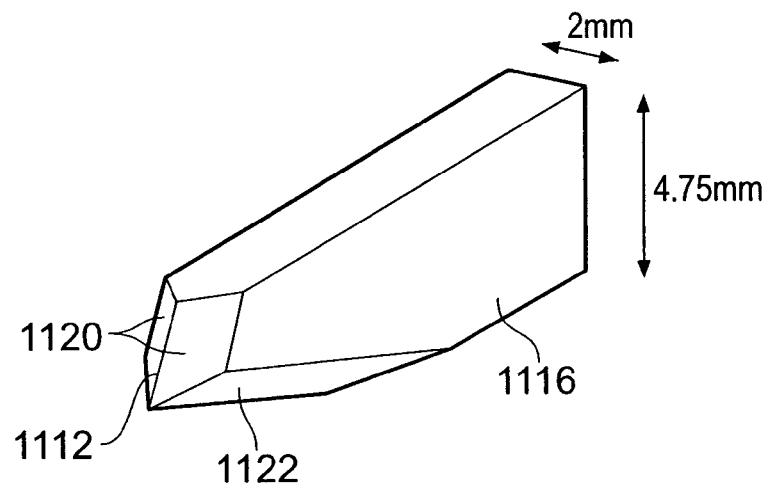
FIG. 26 is a perspective view of the blade structure shown in FIG. 25.

As illustrated in FIG. 26, the rectangular block 1116 has a height of 4.75 mm and a width of 2 mm. Each cutting edge is symmetrical about the longitudinal mid-plane of the blade structure (i.e. the plane through the middle of the blade parallel with the plane of the paper in FIG. 25). The angle made by the faces which meet along each cutting edge 1112, 1114 is 90°. Altering this angle can change the location of the area of main power absorption in the tissue. Making it less than 90° (i.e. a sharper edge) may move the area of main heating back from the edge towards the blade structure.

Referring again to FIG. 25, the upper cutting edge 1112 is at an angle of 60° with respect to the top surface of the blade structure and the lower cutting edge 1114 is at an angle of 15° with respect to the bottom surface of the blade structure. The cutting edges 1112, 1114 meet at a blade tip 1118 that is half way up the height of the rectangular block.

The sides of the rectangular block 1116 (i.e. the side surfaces and top and bottom surfaces) are metallised. The angled faces 1120, 1122 which meet at the cutting edges 1112, 1114 respectively are not metallised; the alumina is exposed at this position.

The dimensions for the radiating blade structure are obtained based on information about the overall structure of the surgical resection tool. The surgical resection tool may comprise the following components:
- a microwave connector assembly to connect the surgical resection tool to a microwave source;
- a cable assembly to transfer energy from the microwave source to the radiating blade structure (e.g. a co-axial cable or a suitable waveguide);
- an impedance matching circuit (or transformer) to match the impedance of the cable assembly to the tissue impedance; and
- the radiating blade structure itself.

The impedance matching transformer may be integrated with the blade structure.

In some embodiments for implementing the surgical resection tool, rectangular waveguide cable has been used as the cable assembly. The waveguide cable may be flexible/twistable. The design of the surgical blade depends on the size of the waveguide cavity, which in turn depends on the range of frequencies that the waveguide is able to support. Table 1 provides a list of standard waveguide cavities along with physical dimensions for the waveguide cavity and the frequency range over which the waveguide cavities can be used.

If the cavity size is smaller than that required for the operating frequency range then the electromagnetic fields will not propagate inside the waveguide or the wave will be cut-off. The embodiment shown in FIG. 25 uses radiation at a frequency of 24 GHz. A spot frequency of 14.5 GHz is used in an embodiment discussed below. The following standard waveguides may be employed to propagate the energy in such embodiments: waveguide 17 (WR75), waveguide 18 (WR62), waveguide 20 (WR42), and waveguide 21 (WR34). These waveguides can enable dominant mode ($TE_{10}$) operation at 14.5 GHz (WR75 and WR62) and 24 GHz (WR42 and WR34).

TABLE 1

Standard waveguide characteristics

| Waveguide type | Frequency range (GHz) | Outer dimensions and wall thickness (mm) | Cut-off wavelength for $TE_{10}$ mode (mm) | Cut-off frequency for $TE_{10}$ mode (GHz) |
| --- | --- | --- | --- | --- |
| WR187 (WG12) | 3.95-5.85 | 50.8 × 25.4 × 1.626 | 95.0 | 3.16 |
| WR159 (WG13) | 4.90-7.05 | 43.64 × 23.44 × 1.626 | 80.9 | 3.71 |
| WR137 (WG14) | 5.85-8.20 | 38.1 × 19.05 × 1.626 | 69.8 | 4.29 |
| WR112 (WG15) | 7.05-10.0 | 31.75 × 15.88 × 1.626 | 57.0 | 5.26 |
| WR90 (WG16) | 8.20-12.4 | 25.4 × 12.7 × 1.27 | 45.7 | 6.26 |
| WR75 (WG17) | 10.0-15.0 | 21.59 × 12.07 × 1.27 | 38.1 | 7.88 |
| WR62 (WG18) | 12.4-18.0 | 17.83 × 9.93 × 1.02 | 31.6 | 9.49 |
| WR42 (WG20) | 18.0-26.5 | 12.7 × 6.35 × 1.02 | 21.3 | 14.1 |
| WR34 (WG21) | 21.7-33.0 | 10.67 × 6.35 × 1.02 | 17.3 | 17.3 |
| WR28 (WG22) | 26.5-40.0 | 9.14 × 5.58 × 1.02 | 14.2 | 21.1 |

It can be seen from the table that the frequency of operation also determines the physical dimensions of the waveguide cavity. In order to realise a surgical instrument with dimensions similar to those of a conventional scalpel blade it can be seen that one should consider using WG20, WG21 or WG22 to successfully implement the surgical resection tool.

Figure 27:
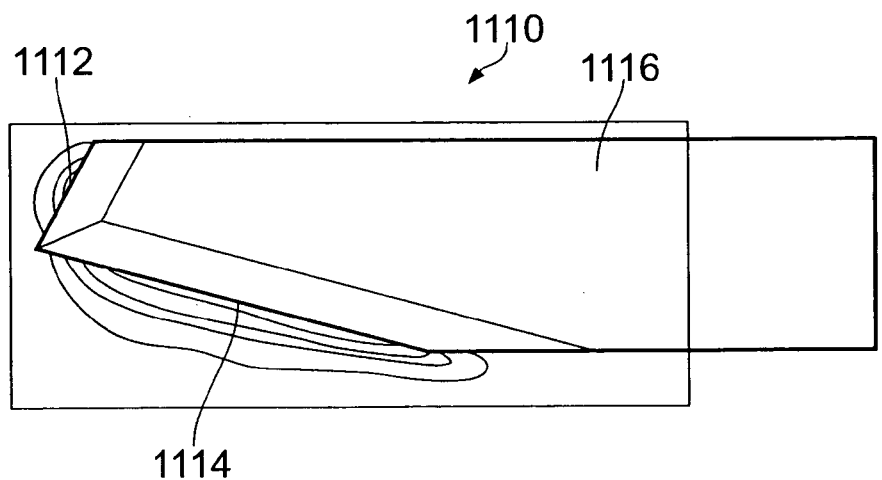
FIG. 27 is a electromagnetic field simulation showing power loss density at the mid-plane of the blade structure shown in FIG. 25 when in liver tissue.

FIG. 27 is a simulation showing the density of power lost from the radiating blade structure 1110 when it is inserted into liver tissue and microwave energy having a frequency of 24 GHz is directed through it. FIG. 27 shows that the power loss (and therefore main area of heating) is focussed along the lower cutting edge 1114, which in this embodiment is the edge used for cutting. Thus, the energy desired e.g. for instant cauterisation at the time of cutting is provided at the target area by this embodiment. The field distribution is also substantially uniform along the length of the cutting edge. Moreover, no extraneous power absorption is shown, i.e. no substantial heating occurs at other locations with respect to the blade structure, so unwanted (potentially damaging) side effects may be avoided.

Figure 28:
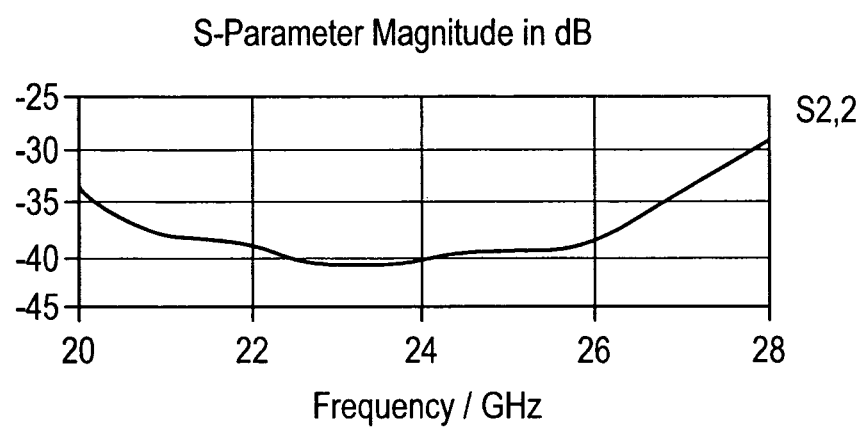
FIG. 28 is a graph showing return loss of the blade structure shown in FIG. 25 when in liver tissue over a range of frequencies.

FIG. 28 shows the return loss of the blade structure into liver tissue over a range of frequencies. Over the range of frequencies simulated (20-28 GHz), the return loss (i.e. measure of match) between the blade and the tissue is better than (more negative than) −30 dB, which indicates that more than 99.9% of energy delivered from the radiating section will be delivered into the tissue. Since the complex impedance of blood is very similar to that of liver, the match into blood will also be very good.

Figure 29:
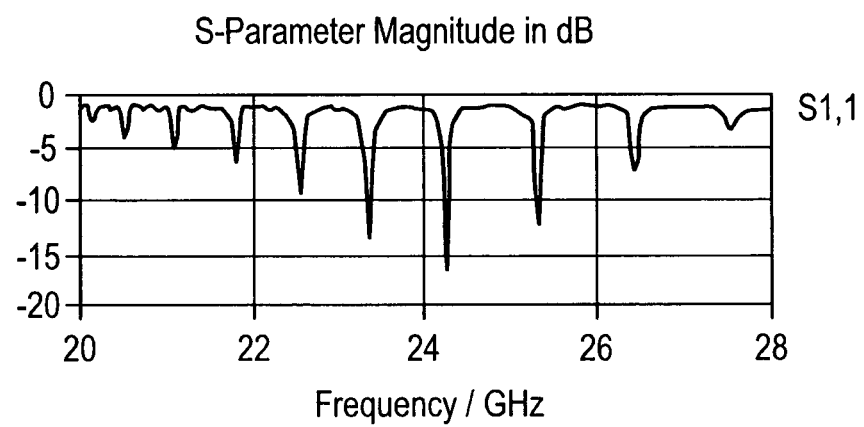
FIG. 29 is a graph showing return loss of the blade structure shown in FIG. 25 when in air over a range of frequencies.

FIG. 29 shows the return loss of the blade structure into air. Over the frequency range simulated (20-28 GHz), the return loss is generally above (more positive than) −5 dB. The graph shows that resonance occurs at various frequencies. This is caused by extra modes generated by reflections at the blade tip that are not absorbed at the other end (feed end) of the blade structure and therefore reflect back and forth. At the target frequency (24 GHz) the return loss is above (more positive than) −1 dB. For extra safety it may be desirable for the power supplied to the blade structure to be reduced when the return loss has a magnitude less than (i.e. is more positive than) −3 dB (where return loss may be defined as −20 $\log_{10}|\Gamma|$, where $\Gamma$ is the reflection coefficient, i.e. a measure of the ratio of the power delivered into tissue to the power coming back due to a mismatch in impedance).

Figure 30:
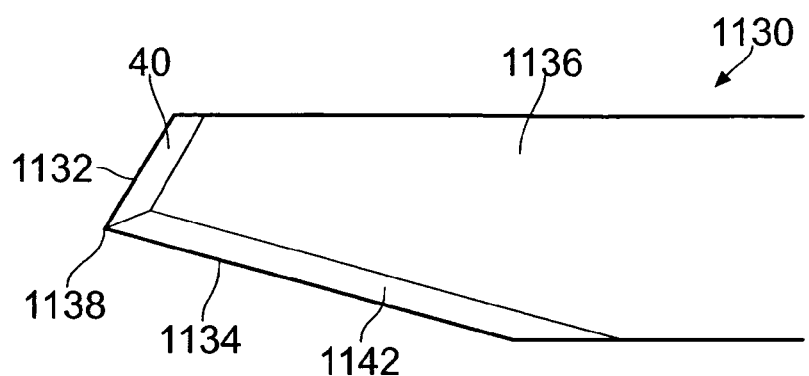
FIG. 30 is a side view of a blade structure that is yet another embodiment of the invention.
Figure 31:
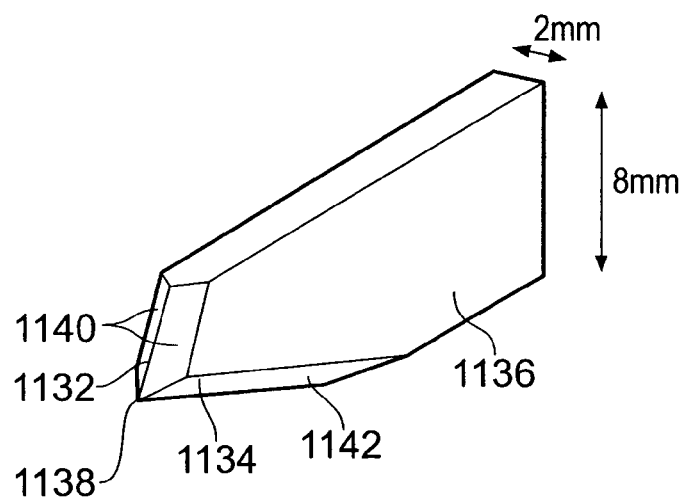
FIG. 31 is a perspective view of the blade structure shown in FIG. 30.
Figure 32:
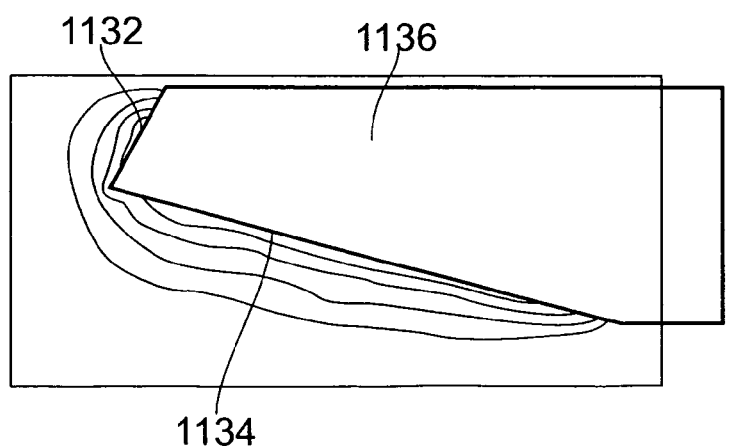
FIG. 32 is a electromagnetic field simulation showing power loss density at the mid-plane of the blade structure shown in FIG. 30 when in liver tissue.

FIGS. 30 to 32 are representations corresponding to FIGS. 25 to 27 but for a radiating blade structure 1130 for another embodiment of a surgical antenna, this time being particularly suitable for operation at 14.5 GHz. The shape of the blade structure 1130 is similar to the blade structure 1110 shown in FIG. 25. There are two angled cutting edges 1132, 1134 machined into one end of a rectangular block 1136. The dimensions of the rectangular block are different in this embodiment. As shown in FIG. 31, the rectangular block has a width of 2 mm and a height of 8 mm. Other details are the same, however. For example, upper cutting edge 1132 makes an angle of 60° with the top surface of the rectangular block 1136, while lower cutting edge 1134 makes an angle of 15° with the bottom surface of the rectangular block 1136. These angles were chosen because they are representative of standard surgical scalpel blades that are commonly used by surgeons or clinicians. The cutting edges 1132, 1134 meet at a blade tip 1138 which is half way up the height of the rectangular block 1136. The angled surfaces 1140, 1142 which meet at the cutting edges 1132, 1134 respectively are at 90° to each other. The side surfaces and top and bottom surfaces of the rectangular block 1136 are metallised, but the angled surfaces 1140, 1142 are not metallised (i.e. are exposed alumina).

FIG. 32 is a simulation of power loss from the blade structure when in liver tissue and having microwave energy with a frequency of 14.5 GHz delivered thereto. As for the previous embodiment, the power absorption is localised at and evenly distributed along the cutting edges 1132, 1134.

Figure 33:
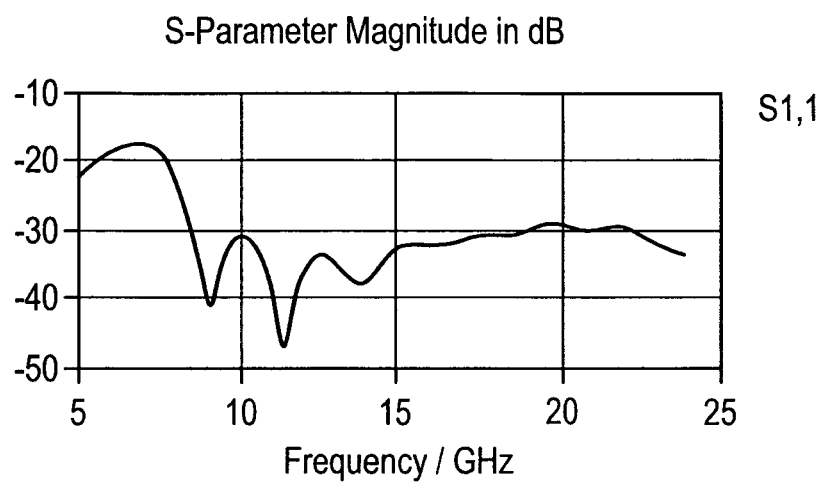
FIG. 33 is a graph showing return loss of the blade structure shown in FIG. 30 when in liver tissue over a range of frequencies.

FIG. 33 is a graph showing the return loss of the blade structure into liver tissue over a range of frequencies. At the frequency of interest (14.5 GHz) the return loss (i.e. measure of match) between the blade and the tissue is better than (more negative than) −30 dB, which indicates that more than 99.9% of energy delivered from the radiating section will be delivered into the tissue.

A second (albeit independent) feature of each of the embodiments disclosed herein is a transformer for connecting the waveguide cavity to the biological tissue with a good match. The arrangement proposed herein is an interface made using dielectric material which can achieve matching without tuning. The dielectric material used to perform the impedance transformation may be the same as that used for the radiating/cutting blade. The transformer and the radiating/cutting blade may form a single section or piece. A good match can avoid undesirable heating at the blade-waveguide connection.

Figure 34:
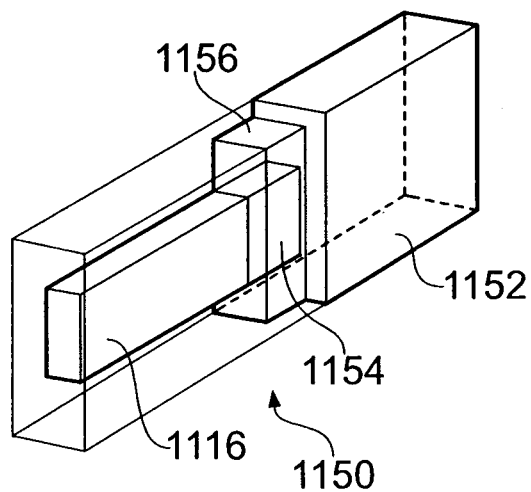
FIG. 34 is a perspective view of a transformer structure suitable for attaching the blade structure shown in FIG. 25 to a waveguide.

FIG. 34 is a perspective view of a transformer 1150 for connecting rectangular block 1116 of the blade structure 1110 shown in FIG. 25 to a waveguide 1152 (e.g. a standard waveguide). The length of the transformer should be an odd multiple of a quarter of the loaded wavelength at the frequency of interest, i.e. $(2n-1)\lambda_L/4$, where n is any integer from 1 to ∞ and $\lambda_L$ is the loaded wavelength that corresponds to the frequency of interest. Due to the fact that it is required to match a waveguide filled with air with a relative permittivity of unity to the tissue load with a high dielectric constant, e.g. 40, it is necessary to form the matching transformer from a material with a high dielectric constant. This leads to a very short loaded wavelength (especially at the higher frequency of 24 GHz). This situation may be best illustrated by way of a worked example:

assume that the waveguide is full of air ($\epsilon_r=1$)
assume that the dielectric constant of the tissue is 40
the dielectric constant for the transformer material can therefore be approximated to $$\sqrt{1\times 40}=6.32.$$

This assumes that the loss factor (tan δ) is close to zero. In practice this is desirable to minimise power loss in the transformer material, which would manifest itself as heat.

for 24 GHz operation, the length of the quarter wavelength impedance transformer is given by $$\frac{c}{f\times 4\times \sqrt{6.32}},$$

where c is the speed of light in m/s and f is the frequency of operation in Hertz. Applying this equation in the present example yields a quarter wavelength of 1.24 mm.

This length may be impractical, so an odd multiple may be used, e.g. $3\lambda_L/4=3.72$ mm or even $5\lambda_L/4=6.2$ mm.

A un-metallised end section 1154 of the rectangular block 1116 projects through the centre of a waveguide transformer section 1156 which has dimensions chosen based on the size of the rectangular block 1116, waveguide 1152 and frequency of microwave energy delivered to provide a match between the rectangular block 1116 and waveguide 1152. In this embodiment, where the operating frequency is 24 GHz, the waveguide transformer section 1152 has a simulated length of 5.9 mm (the un-metallised end section 54 projects along the entirety of this length), a height of 10 mm and a width of 3.2 mm. This section can join straight onto (and indeed be machined from the end of) a waveguide 52 of 4.318 mm 10.668 mm cross-section. The transformer may be provided in a handle section of the surgical antenna.

Figure 35:
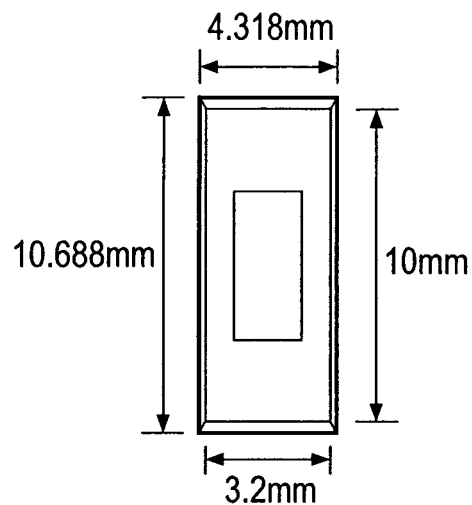
FIG. 35 is a front view of the transformer shown in FIG. 34.

FIG. 35 is a cross-sectional view through the waveguide transformer section 1156 looking towards the waveguide 1152. The dimensions used in this embodiment are shown in the drawing.

Figure 36:
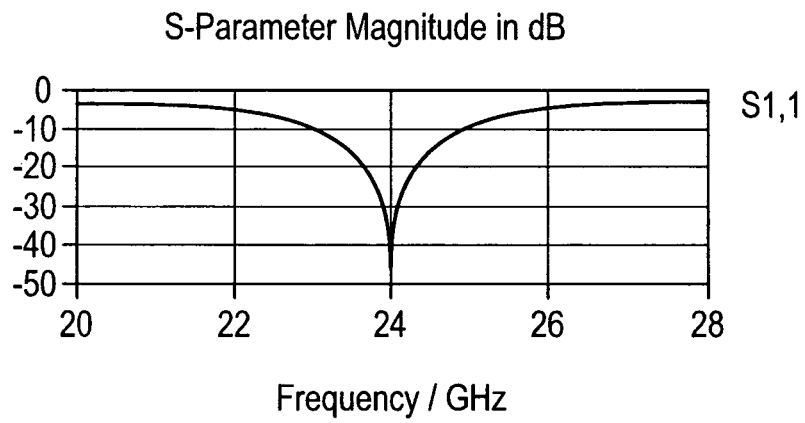
FIG. 36 is a graph showing return loss of the transformer shown in FIG. 34 from a waveguide.

FIG. 36 is a graph showing the return loss of the transformer 1150. At 24 GHz the return loss is much better (more negative) than −30 dB, which indicates that more than 99.9% of microwave energy delivered into the transformer 1150 will be delivered into the blade structure 1110.

Figure 37:
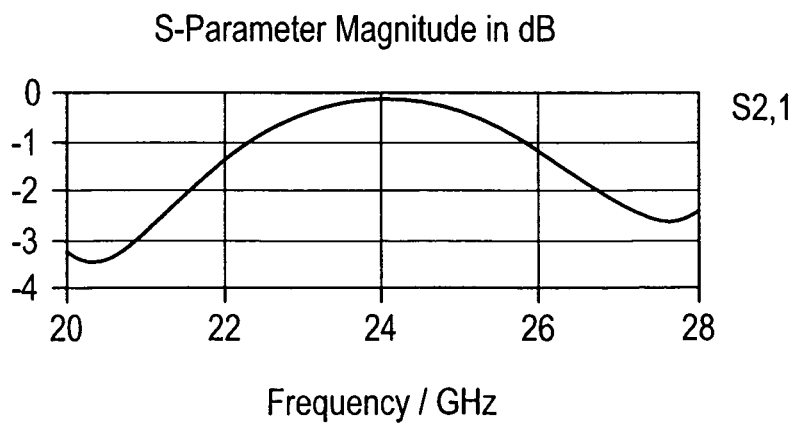
FIG. 37 is a graph showing insertion loss of the transformer shown in FIG. 34 from a waveguide.

FIG. 37 is a graph showing the insertion loss of the transformer 1150. At 24 GHz the insertion loss is better (more negative or less than) than 0.2 dB, i.e. 0.1 dB, which indicates that a large proportion of the energy delivered from the waveguide 1152 enters the transformer 1150. The transformer has been designed with the radiating blade immersed inside a block of tissue that is representative of the liver/blood load. When the load changes, i.e. to that of air for example, the matching transformer will not enable a good match to be made between the radiating blade and the tissue load, hence a large portion of the energy will be reflected back into the waveguide and along the cable assembly.

Figure 38:
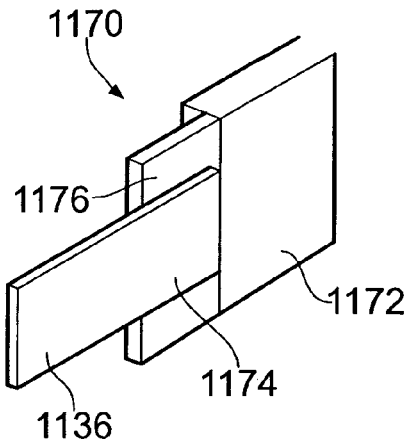
FIG. 38 is a perspective view of a longitudinal cross-section through a transformer structure suitable for attaching the blade structure shown in FIG. 30 to a waveguide.
Figure 39:
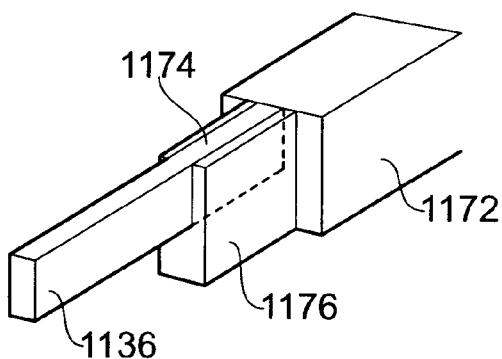
FIG. 39 is a perspective view of a lateral cross-section through the transformer structure shown in FIG. 38.

FIGS. 38 and 39 are cross-sectional views through a transformer 1170 for connecting rectangular block 1136 of the is blade structure 1130 shown in FIG. 30 to a waveguide 1172 (e.g. a standard waveguide such as WG 18). The arrangement shown in FIGS. 38 and 39 is similar to FIGS. 34 and 35 except for different dimensions to provide a match for a differently sized rectangular block 1136 and a different operation frequency (in this case 14.5 GHz). In this embodiment, an un-metallised end section 1174 of the rectangular block 1136 projects through a waveguide transformer section 1176 that is an integral end part of the waveguide 1172. As above, the dimensions of the arrangement are chosen based on the size of the rectangular block 36, waveguide 1172 and frequency of microwave energy delivered to provide a match between the rectangular block 1136 and waveguide 1172. In this embodiment, where the operating frequency is 14.5 GHz, the waveguide transformer section 1176 has length of 12 mm (the un-metallised end section 1174 projects along the entirety of this length), a height of 15.4 mm and a width of 3.6 mm.

Figure 40:
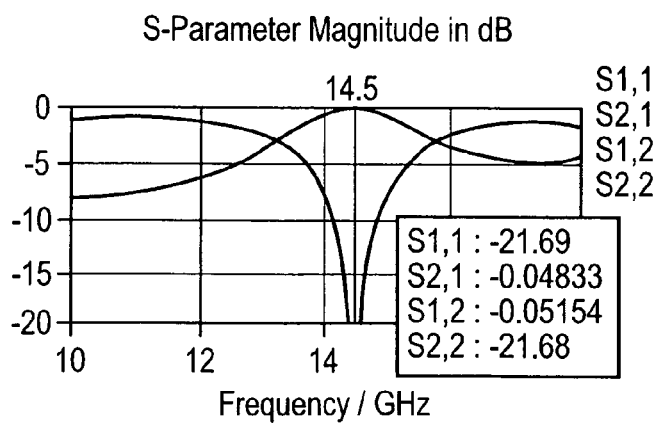
FIG. 40 is a graph showing return loss and insertion loss of the transformer shown in FIG. 38 from a waveguide.

FIG. 40 is a graph showing the return loss and insertion loss of the transformer 1170. At 14.5 GHz the return loss is better (more negative) than −20 dB, which indicates that more than 99% of microwave energy delivered into the transformer 1170 will be delivered into the blade structure 1130. At 14.5 GHz the insertion loss is better (more negative or less than) than 0.1 dB, i.e. 0.05 dB which indicates that a substantial majority of the energy delivered from the waveguide 1172 enters the transformer 1170.

The invention claimed is:

1. A surgical instrument having:
   a waveguide for carrying microwave energy having a frequency between 5 GHz and 100 GHz; and
   a cutting element connected to the waveguide to receive the microwave energy therefrom, the cutting element comprising a piece of dielectric material configured to load the waveguide, wherein the piece of dielectric material includes:
   a sharpened edge forming a blade for cutting biological tissue;
   a radiating antenna for emitting the microwave energy as a microwave radiation field from the sharpened edge into the biological tissue; and
   an impedance transformer arranged to provide substantially maximum field coupling from the waveguide to the cutting element, the impedance transformer being integrally formed with the cutting element and arranged to match a first impedance, which is an impedance of the waveguide before it is loaded with the piece of dielectric material, with a second impedance, which is a predetermined impedance of the biological tissue,
   wherein the piece of dielectric material comprises a piece of ceramic having a metallised surface except for a first unmetallised region at a proximal coupling portion and a second unmetallised region at the sharpened edge,
   wherein the radiating antenna is formed by the second unmetallised region, and
   wherein the impedance transformer is located between the waveguide and the sharpened edge.

2. The surgical instrument according to claim 1, wherein the impedance transformer is a tapered transformer or a step transformer.

3. The surgical instrument according to claim 1, further including a stub tuner in the waveguide.

4. The surgical instrument according to claim 1, wherein the ceramic is alumina or sapphire.

5. The surgical instrument according to claim 1, wherein the microwave radiation field is substantially uniform along the blade.

6. The surgical instrument according to claim 1 including a tuning mechanism arranged to adjust the first impedance.

7. The surgical instrument according to claim 6, wherein the tuning mechanism includes three screws adjustably mounted in the waveguide.

8. The surgical instrument according to claim 1, wherein the impedance transformer has a length in a direction along the waveguide that is an odd multiple of a quarter of a wavelength of the microwave radiation that is configured to propagate in the waveguide.

9. A surgical cutting apparatus having:
   a microwave source arranged to generate microwave energy having a stable frequency between 5 GHz and 100 GHz; and
   a surgical instrument having:
     a waveguide connected to receive the microwave energy from the microwave source, and
     a cutting element connected to the waveguide to receive the microwave energy therefrom, the cutting element comprising a piece of dielectric material configured to load the waveguide, wherein the piece of dielectric material includes:
       a sharpened edge forming a blade for cutting biological tissue;
       a radiating antenna for emitting the microwave energy as a microwave radiation field at the sharpened edge into the biological tissue; and
       an impedance transformer arranged to provide substantially maximum field coupling from the waveguide to the cutting element, the impedance transformer being integrally formed with the cutting element and arranged to match a first impedance, which is an impedance of the waveguide before it is loaded with the piece of dielectric material, with a second impedance, which is a predetermined impedance of the biological tissue,
     wherein the piece of dielectric material comprises a piece of ceramic having a metallised surface except for a first unmetallised region at a proximal coupling portion and a second unmetallised region at the sharpened edge,
     wherein the radiating antenna is formed by the second unmetallised region, and
     wherein the impedance transformer is located between waveguide and the sharpened edge.

10. The surgical cutting apparatus according to claim 9 including:
    a reflected radiation detector connected between the microwave source and the surgical instrument; and
    an impedance adjuster connected between the microwave source and the surgical instrument;
    wherein the reflected radiation detector is arranged to detect a magnitude and a phase of microwave radiation reflected back through the surgical instrument towards the microwave source, and the impedance adjuster has an adjustable complex impedance that is controllable based on the detected magnitude and phase of the reflected microwave radiation.

11. The surgical cutting apparatus according to claim 10 including forward and reflected power directional couplers arranged to detect the microwave radiation between the surgical instrument towards the microwave source, wherein the reflected radiation detector is a heterodyne receiver arranged to extract both magnitude and phase information from the microwave radiation coupled by the forward and reflected power directional couplers.

12. The surgical cutting apparatus according to claim 11, wherein the impedance adjuster is dynamically adjustable based on the phase and magnitude information extracted by the reflected radiation detector.

\* \* \* \* \*